(12) United States Patent
Fegelman et al.

(10) Patent No.: US 7,549,853 B2
(45) Date of Patent: *Jun. 23, 2009

(54) APPARATUS FOR MAKING AIR-LAID STRUCTURES

(75) Inventors: Karen Juliana Fegelman, Cincinnati, OH (US); Claudio Antonio Matos, Belleville (CA); Curtis Hunter Van Valkenburgh, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 232 days.

This patent is subject to a terminal disclaimer.

(21) Appl. No.: 11/599,820

(22) Filed: Nov. 15, 2006

(65) Prior Publication Data

US 2008/0113054 A1    May 15, 2008

(51) Int. Cl.
B29C 41/40 (2006.01)
A61F 13/15 (2006.01)
B29C 41/22 (2006.01)

(52) U.S. Cl. .................... 425/80.1; 425/81.1; 425/82.1; 425/83.1; 425/215

(58) Field of Classification Search ............... 425/72.1, 425/72.2, 80.1, 81.1, 82.1, 83.1, 468, 470, 425/DIG. 2, 215; 264/101–103, 112, 119, 264/121, 211.12, 37.1, 37.17, 37.28, 39, 264/510, 511, 553, 555, 571, 324, 517, 518; 19/144, 145, 148, 308
See application file for complete search history.

(56) References Cited

U.S. PATENT DOCUMENTS

| | | | |
|---|---|---|---|
| 3,518,726 A * | 7/1970 | Banks | 28/121 |
| 3,873,259 A * | 3/1975 | Kennedy | 425/470 |
| 3,973,291 A | 8/1976 | Kolbach | |
| 4,005,957 A * | 2/1977 | Savich | 425/80.1 |
| 4,388,056 A | 6/1983 | Lee et al. | |
| 4,592,708 A | 6/1986 | Feist et al. | |
| 4,666,647 A | 5/1987 | Enloe et al. | |
| 4,674,966 A | 6/1987 | Johnson et al. | |
| 4,761,258 A | 8/1988 | Enloe | |

(Continued)

OTHER PUBLICATIONS

U.S. Appl. No. 11/599,789, filed Nov. 15, 25006, C. H. Van Valkenburgh et al.

(Continued)

*Primary Examiner*—Philip C Tucker
*Assistant Examiner*—Dimple N Bodawala
(74) *Attorney, Agent, or Firm*—Gary J. Foose

(57) ABSTRACT

An apparatus for forming air-laid fibrous articles. The apparatus can have a core pocket operatively related with an air-distribution manifold that can apply different air pressures to different portions of the core pocket. The core pocket can have a shield and a central opening defined by a void in the shield. The core pocket can have a central forming chamber in air-flow communication with the central opening and have a central forming chamber periphery. The core pocket can have a central foraminous forming surface in air-flow communication with the central forming chamber. The core pocket can have a pair of edge openings extending along the shield. The core pocket can have an edge forming chamber disposed about the central forming chamber periphery and in air-flow communication with the edge openings. The core pocket can have an edge foraminous forming surface in air-flow communication with the edge forming chamber.

20 Claims, 12 Drawing Sheets

U.S. PATENT DOCUMENTS

| | | | |
|---|---|---|---|
| 4,859,388 A | 8/1989 | Peterson et al. | |
| 4,888,231 A | 12/1989 | Angstadt | |
| 4,904,440 A | 2/1990 | Angstadt | |
| 4,995,141 A * | 2/1991 | Gould | 19/148 |
| 5,004,579 A | 4/1991 | Wislinski et al. | |
| 5,447,677 A | 9/1995 | Griffoul et al. | |
| 5,866,173 A * | 2/1999 | Reiter et al. | 425/80.1 |
| 6,098,249 A * | 8/2000 | Toney et al. | 19/296 |
| 6,146,580 A | 11/2000 | Bontaites, Jr. | |
| 6,330,735 B1 * | 12/2001 | Hahn et al. | 19/296 |
| 6,416,697 B1 * | 7/2002 | Venturino et al. | 264/113 |
| 6,461,086 B1 * | 10/2002 | Milanowski et al. | 406/92 |
| 6,497,009 B2 * | 12/2002 | Geisen et al. | 19/296 |
| 6,627,130 B2 * | 9/2003 | Kugler et al. | 264/118 |
| 6,630,088 B1 | 10/2003 | Venturino et al. | |
| 6,630,096 B2 | 10/2003 | Venturino et al. | |
| 6,652,798 B1 | 11/2003 | Edvardsson | |
| 6,736,923 B1 | 5/2004 | Franzmann et al. | |
| 6,811,642 B2 | 11/2004 | Ochi | |
| 6,846,448 B2 * | 1/2005 | Rymer et al. | 264/460 |
| 7,001,167 B2 * | 2/2006 | Venturino et al. | 425/80.1 |
| 7,094,373 B2 * | 8/2006 | Heyn et al. | 264/101 |
| 7,157,033 B2 * | 1/2007 | Kuchenbecker et al. | 264/162 |
| 7,204,682 B2 * | 4/2007 | Venturino et al. | 425/82.1 |
| 2002/0013112 A1 | 1/2002 | Bontaites, Jr. et al. | |
| 2002/0070471 A1 | 6/2002 | Lee et al. | |
| 2004/0023583 A1 | 2/2004 | Venturino et al. | |
| 2004/0061264 A1 * | 4/2004 | Heyn et al. | 264/518 |
| 2008/0113052 A1 * | 5/2008 | Van Valkenburgh et al. | 425/2 |

OTHER PUBLICATIONS

U.S. Appl. No. 11/599,821, filed Nov. 15, 2006, C A. Matos et al.
U.S. Appl. No. 11/599,843, filed Nov. 15, 2006, C. H. Van Valkenburgh et al.

* cited by examiner

APPARATUS FOR MAKING AIR-LAID STRUCTURES

FIELD OF THE INVENTION

The present invention relates to an apparatus for making air-laid articles.

BACKGROUND OF THE INVENTION

Air-laid structures are widely used in the art of absorbent articles and other arts in which fibrous webs are of use. One common approach for creating air-laid structures is to process a fibrous sheet of cellulosic fibers or other suitable fibers through a device that breaks up the fibrous sheet, thereby forming discrete fibers. The discrete fibers are entrained in a stream of air and directed to a foraminous forming surface upon which the fibers are deposited to form fluff. Typically, fluff has a high porosity and is comprised of essentially randomly oriented fibers. In some processes, a vacuum is applied to one side of the foraminous surface to create a pressure differential across the foraminous forming surface to assist with drawing the discrete fibers to the foraminous forming surface.

Absorbent articles such as sanitary napkins, diapers, and adult incontinence products commonly employ air-laid structures in the absorbent core. Absorbent cores have a generally planar structure in which the thickness is generally smaller than the planar dimensions. One common approach to forming air-laid absorbent articles is to situate the foraminous surface in a recess. In the art, the structure in which the foraminous surface is emplaced and the foraminous surface are components of what is commonly referred to as a core pocket. The thickness can be partially controlled by the depth of the recess in the core pocket and the planar dimensions of the absorbent core can be defined by the dimensions of the recess and the foraminous surface Absorbent cores comprised of two or more different fibrous materials deposited in two different zones in which one fibrous material is deposited as an island surrounded by a second fibrous material may be useful. Creating an absorbent core having an island of one fibrous material surrounded by a second fibrous material without significant intermixing and layering of different fibrous materials can be difficult to accomplish on a commercial scale.

With these limitations in mind, the problem remains with providing an apparatus to manufacture air-laid fibrous articles comprised of an island of a first fibrous material surrounded by a second fibrous material without significant intermixing and layering of different fibrous materials that can be used on a commercial scale.

SUMMARY OF THE INVENTION

An apparatus for forming air-laid fibrous articles is disclosed. The apparatus can comprise a core pocket and an air-distribution manifold operatively related to the core pocket. The core pocket can comprise a shield having an interior facing surface, an exterior facing surface, a shield first end, a shield second end opposing the shield first end, and a pair of opposing shield lateral side edges extending from the shield first end to the shield second end. The core pocket can further comprise a central opening defined by a void in the shield. The core pocket can further comprise a central forming chamber in air-flow communication with the central opening and having a central forming chamber periphery. The core pocket can further comprise a central foraminous forming surface in air-flow communication with the central forming chamber. The core pocket can further comprise a pair of edge openings extending along the shield and extending laterally beyond the shield lateral side edges. The core pocket can further comprise an edge forming chamber disposed about the central forming chamber periphery and in air-flow communication with the edge openings. The core pocket can further comprise an edge foraminous forming surface in air-flow communication with the edge forming chamber.

The core pocket can further comprise a plurality of central lateral baffles. The central lateral baffles can span the central forming chamber. The central lateral baffles can be aligned about flush with the interior facing surface of the shield.

The core pocket can further comprise a plurality of edge lateral baffles. The edge lateral baffles can span the edge forming chamber. The edge lateral baffles can be aligned about flush with the interior facing surface of the shield.

The air-distribution manifold can comprise a second forming area. The second forming area can comprise a second central zone. The second central zone can have a second central zone first end, a second central zone second end opposing the second central zone first end, and a pair of opposing second central zone lateral side edges extending from the second central zone first end to the second central zone second end. The second forming area can comprise a pair of second edge zones, each of the second edge zones adjacent a second central zone lateral side edge.

The second central zone and the second edge zones can be under pressure and the pressure in the second central zone can be negative and less than the pressure in the second edge zones. The pressure in the second edge zones can be negative and less than the pressure in the second central zone.

The apparatus can further comprise a first forming area. The first forming area can comprise a first central zone. The first central zone can have a first central zone first end, a first central zone second end opposing the first central zone first end, and a pair of opposing first central zone lateral side edges extending from the first central zone first end to the first central zone second end, wherein the first central zone second end is adjacent the second central zone first end. The first forming area can further comprise a pair of first edge zones, each of the first edge zones adjacent a first central zone lateral side edge.

The first central zone and the first edge zones can be under pressure and the pressure in the first central zone can be negative and the pressure in the first edge zones can be positive. The pressure in the first central zone can be positive and the pressure in the first edge zones can be negative.

The air-distribution manifold can further comprise a cleaning area. The cleaning area can comprise a central cleaning zone. The central cleaning zone can have a central cleaning zone first end, a central cleaning zone second end opposing the central cleaning zone first end, and a pair of opposing central cleaning zone lateral side edges extending from the central cleaning zone first end to the central cleaning zone second end. The central cleaning zone second end can be adjacent the second central zone first end. The air-distribution manifold can further comprise a pair of edge cleaning zones. Each of the edge cleaning zones can be adjacent a central cleaning zone lateral side edge.

The central cleaning zone and edge cleaning zones can be under pressure and the pressure in the central cleaning zone can be positive and the pressure in the edge cleaning zones can be negative. The pressure in the central cleaning zone can be negative and the pressure in the edge cleaning zones can be positive.

The first central zone second end can be adjacent the central cleaning zone first end. The pressure in the first central zone can be negative.

The edge cleaning zones can have an edge cleaning zone first end and an edge cleaning zone second end opposing the edge cleaning zone first end.

The first forming area can comprise a pair of first edge zones. Each of the first edge zones can be adjacent an edge cleaning zone first end. The pressure in the first edge zones can be negative.

The apparatus can further comprise a first discharge chute that discharges first fibers and a second discharge chute that discharges second fibers. The first fibers can differ from the second fibers. The first discharge chute and the second discharge chute can be operatively related to the core pocket and the air-distribution manifold.

The first fibers and the second fibers can differ from one another in terms of their fluid handling properties. The first fibers and the second fibers differ from one another in a manner selected from the group consisting of color, a tactile property, and a mechanical property.

The core pocket can be shaped to form an absorbent article designed to be worn in proximity to the crotch of the wearer. The core pocket can be shaped to form the core of a sanitary napkin.

DETAILED DESCRIPTION OF THE INVENTION

Figure 1:
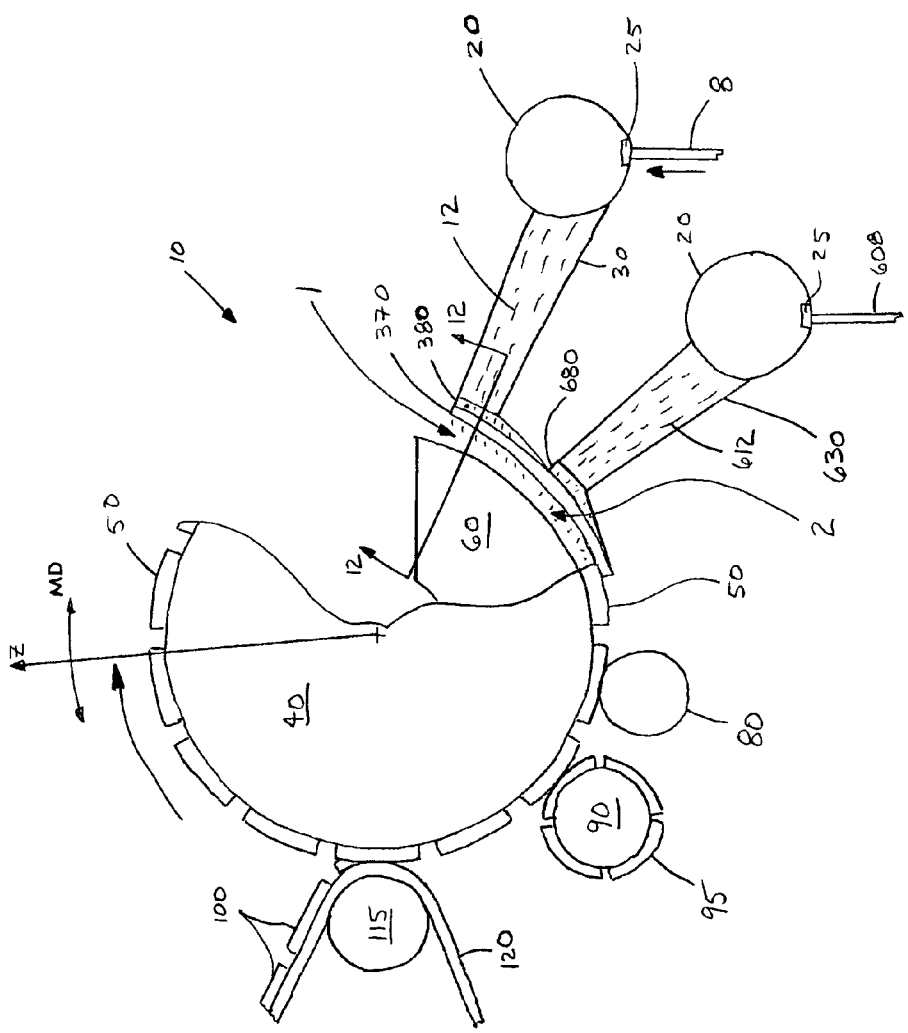
FIG. 1 is an illustration of a side view of one embodiment of an apparatus for forming air-laid fibrous articles.

An illustration of one embodiment of an apparatus 10 for forming air-laid fibrous articles is shown in FIG. 1. The apparatus 10 can comprise hammermills 20, or other suitable apparatus such as a disk mill or lickerin or other apparatus for disassociating fibers of a drylap web, into which a drylap web 8 can be fed through an infeed slot 25. A first drylap web 8 can be fed into one of the hammermills 20 and a second drylap web 608 into another hammermill 20. The drylap webs are fed into the hammermills 20 through infeed slot 25. The hammermills 20 disassociate the fibers of the drylap webs and then discharge relatively high velocity streams of loose air-entrained fibers that are directed through discharge chutes generally towards a core pocket 50. The disassociated first fibers 12 of the first drylap web 8 are directed through and discharged through first discharge chute 30 and the disassociated second fibers 612 of the second drylap web 608 are directed through and discharged through second discharge chute 630. A first fiber source entrance chamber 380 can be connected to the first discharge chute 30 assist with distributing the first fibers 12 over the core pocket 50. A second fiber source entrance chamber 680 can be connected to the second discharge chute 630 to assist with distributing the second fibers 612 over the core pocket 50. Non-fibrous materials can be used in place of the first fibers 12 and second fibers 612 provided that the non-fibrous materials used can be conveyed or directed by the flow of air. Non-fibrous materials can include, but are not limited to, pellets, powders, chunks, and shreds of non-fibrous materials.

One or more core pockets 50 can be disposed in a circumferential relationship about the periphery of deposition drum 40. The core pockets 50 can have a foraminous forming surface. Deposition drum 40 can rotate about air-distribution manifold 60. Air-distribution manifold 60 can be in air-flow communication with one or more core pockets 50 as deposition drum 40 rotates about air-distribution manifold 60. As the core pocket 50 rotates near or past the first discharge chute 30, air-distribution manifold 60 can apply a vacuum to at least a portion of the core pocket 50. The vacuum combined with the momentum of the first fibers 12 discharged through first discharge chute 30 act to draw and direct, respectively, the air-entrained first fibers 12 into at least a portion of the core pocket 50 as the core pocket 50 rotates about air-distribution manifold 60 through a region near or past the first discharge chute 30. As the air-entrained first fibers 12 impinge upon the portion of the foraminous forming surface of the core pocket 50 to which vacuum is applied, the first fibers 12 are retained on a portion of the foraminous forming surface and the air is pulled through the foraminous forming surface.

After the first fibers 12 are deposited on a core pocket 50, the core pocket 50 can rotate near or past the second discharge chute 630. The air-distribution manifold 60 can apply a vacuum to a portion of the foraminous forming surface of the core pocket 50 that is without first fibers 12. This vacuum combined with the momentum of the second fibers 612 discharged through second discharge chute 630 act to draw and direct, respectively, the air-entrained second fibers 612 to the portion of the foraminous forming surface of the core pocket 50 that is without first fibers 12.

Other embodiments of the apparatus 10 are possible in which the air-distribution manifold 60 has a different shape from that shown in FIG. 1 and the core pockets 50 are moved across air-distribution manifold 60 by other means. For instance, the air-distribution manifold 60 may have a flat air-distribution surface and core pockets having a flat surface in the machine direction may be slid across the air-distribution manifold 60 by a conveyor system. The core pocket 50 can be described as being in slideable and sealable engagement with the air-distribution manifold.

The core pocket 50 can be slightly overfilled. Scarfing roll 80 can be used to scarf excess fibers deposited in the core pocket 50.

A lugged cylinder 90 can also be an element of the apparatus 10. A plurality of lugs 95 can be disposed about the lugged cylinder 90. The lugs 95 can compact the mass of first fibers 12 and second fibers 612 deposited in the core pocket 50 to complete formation of the air-laid fibrous article 100. The formed air-laid fibrous articles 100 can be removed from the apparatus by a takeaway conveyor comprising a vacuum type return roll 115 and a belt 120. The vacuum type return roll 115 can pull the air-laid fibrous articles 100 from the core pockets 50 as the core pocket 50 rotates past the vacuum type return roll 115.

The apparatus 10 can have two sources of different fibers so that the first fibers 12 can differ from the second fibers 612. The first fibers 12 and second fibers 612 can have different colors. The first fibers 12 and second fibers 612 can differ from one another in their fluid handling properties. Fluid handling properties include, but are not limited to, capillary pressure function, relative permeability function, saturated permeability, irreducible fluid saturation, maximum fluid saturation, fluid-fiber contact angle, and Po. Fluid-fiber contact angle can be used to characterize the hydrophobicity or hydrophilicity of a fiber. The first fibers 12 and second fibers 612 can differ from one another in a tactile property. The first fibers 12 can be a first color and the second fibers 612 can be a second color that differs from the first color. The first fibers 12 and second fibers 612 can differ from one another in their chemical composition. The first fibers 12 and second fibers 612 can differ from one another in a mechanical property. Mechanical properties can include, but are not limited to modulus, Poisson's ratio, and plasticity behavior.

The apparatus 10 can have a first forming region 1 and a second forming region 2. The first forming region 1 and second forming region 2 can be local to the source of the first fibers 12 and the source of the second fibers 612, respectively, and can be local to a core pocket 50 as a core pocket 50 passes though the first forming region 1 and second forming region 2. The forming regions are the portions of the apparatus 10 in which fibers are deposited in the core pocket 50.

The apparatus 10 can further comprise forming zone shields 370. Forming zone shields 370 can be configured such that as the core pocket 50 moves through the forming zone 1, the amount of air flow into the core pocket 50 from the surrounding environment is negligible. In other words, the core pocket 50 can be described as being in slideable and sealable engagement with the forming zone shields 370. Forming zone shields 370 are described more fully herein.

The core pocket 50, and the elements thereof, can be considered to have a machine direction MD. The machine direction can be understood to be the direction in which the core pocket 50 travels as air-laid fibrous articles 100 are formed in the core pocket 50. In the apparatus illustrated in FIG. 1, the machine direction would be in line with the direction of rotation of deposition drum 40. The z direction can be referred to as the direction corresponding with the thickness of the air-laid fibrous article during formation.

U.S. Pat. No. 4,388,056, issued to Lee et al., U.S. Pat. No. 4,859,388, issued to Peterson and Benson, and U.S. Pat. No. 4,592,708 issued to Feist et al. illustrate apparatus for forming air-laid fibrous webs and absorbent articles.

Figure 2:
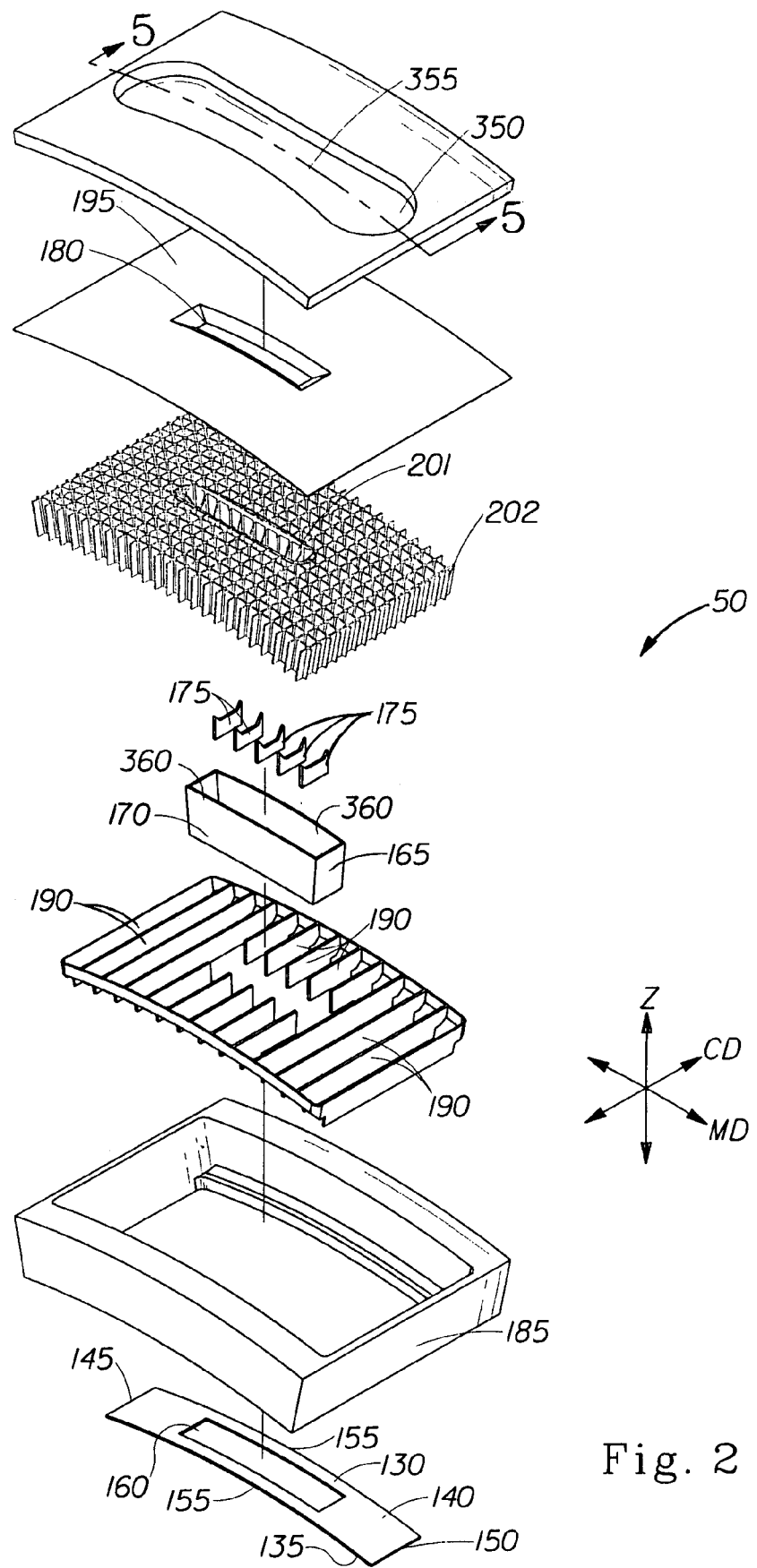
FIG. 2 is an exploded view of a core pocket.

An exploded view of an embodiment of a core pocket 50 is shown in FIG. 2. The core pocket 50, and the elements thereof, can be considered to have a machine direction MD, a cross direction CD, and a z direction generally orthogonal to the MD and CD directions. The cross direction is generally orthogonal to the machine direction and generally in plane with the movement of the core pocket 50 as the core pocket 50 travels during formation of air-laid fibrous articles 100. The machine direction and cross direction can be considered to be in the plane of the air-laid fibrous article. For an apparatus 10 in which one or more core pockets 50 move circumferentially about air-distribution manifold 60, the z direction is radially orthogonal to the circumferential path the core pocket 50 travels during formation of the fibrous article 100.

As described herein, the interior facing surfaces or edges are taken to be oriented in a direction away from the first discharge chute 30 and second discharge chute 630 as the core pocket 50 passes the first discharge chute 30 and second discharge chute 630. If an air-distribution manifold 60 is present, interior facing surfaces are oriented towards the air-distribution manifold 60. The exterior facing surface or edges are taken to be oriented in a direction towards the first discharge chute 30 and second discharge chute 630 as the core pocket 50 passes the first discharge chute 30 and second discharge chute 630.

The core pocket 50 can comprise a shield 130 having an interior facing surface 135 and an exterior facing surface 140 opposing the interior facing surface 135. The shield 130 can have a shield first end 145 and a shield second end 150 opposing the shield first end 145. The shield 130 can have a pair of opposing shield lateral side edges 155, each extending from the shield first end 145 to the shield second end 150. The shield 130 can be a sheet of metal, such as stainless steel, or titanium, or other material sufficiently stiff to be used in machinery used in high speed manufacturing operations. As illustrated in FIG. 2, the shield 130, and other components illustrated, can have an arcuate shape in the machine direction for use in an apparatus 10 in which the core pockets 50 are disposed in a circumferential relationship about the periphery of deposition drum 40, like that shown in FIG. 1. The shield 130 and other components of the core pocket 50 can be flat in the machine direction if an air-distribution manifold 60 that is flat in the machine direction is used. By way of example, and not to be limiting, the shield can have a width in the cross direction between the shield lateral side edges 155 between about 60 mm and about 110 mm. By way of example, and not to be limiting, the shield can have a width in the cross direction between the shield lateral side edges 155 between about 60 mm and about 110 mm, a length in the machine direction between about 0.15 and about 0.55 radians, and a thickness in the z direction between about 0.5 mm to about 3 mm.

The core pocket 50 can further comprise a central opening 160 defined by a void in the shield 130. By way of example, and not to be limiting, the central opening 160 can be an approximately rectangular shape having rounded corners and have a length of about 109 mm in the machine direction and width of about 22 mm in the cross direction. Other shapes, lengths, and widths can be practical, the defining feature being that the central opening 160 is sized and dimensioned so as to provide for air-flow communication between the central forming chamber 165 and the air-distribution manifold 60. The length and width of the central opening 160 can be a function of the in-plane geometry of the air-laid fibrous article 100.

The term air-flow communication is used herein to describe the relationship between two elements in which air flow can be conveyed between, among, across, along, or through the two elements.

The core pocket 50 can further comprise a central forming chamber 165. The central forming chamber 165 can be in air-flow communication with the central opening 160. The central forming chamber 165 can also have a central forming chamber periphery 170. The central forming chamber 165 can be sealed to the shield 130 such that airflow passing between the contacting surfaces of the shield 130 and the central forming chamber 165 can be negligible or nonexistent. The central forming chamber 165 can be formed from stainless steel, titanium, or other material suitable for use in high speed manufacturing operations.

The core pocket 50 can further comprise a plurality of central lateral baffles 175. The central lateral baffles 175 can be nested within the central forming chamber 165. The central lateral baffles 175 can span the central forming chamber 165. That is, the central lateral baffles 175 can extend between the sidewalls 360 of the central forming chamber 165. The central lateral baffles 175 can be aligned about flush with the interior facing surface 135 of the shield 130. The central lateral baffles 175 can be formed from sheets of stainless steel, titanium, or other material suitable for use in high speed manufacturing operations. The sheets can be sized and dimensioned to fit within the central forming chamber 165. The central lateral baffles 175 can be oriented generally orthogonal to the machine direction, as shown in FIG. 2. Embodiments in which the central lateral baffles 175 are not oriented generally orthogonal to the machine direction of the core pocket 50 are also contemplated.

The core pocket 50 can further comprise a central foraminous forming surface 180 in air-flow communication with the central forming chamber 165.

As shown in FIG. 2, the core pocket 50 can further comprise an edge forming chamber 185 that is disposed about the central forming chamber periphery 170. The core pocket 50 can further comprise a plurality of edge lateral baffles 190 nested within the edge forming chamber 185. The edge lateral baffles 190 can span the interior of the edge forming chamber 185. The edge lateral baffles 190 can span the space between the interior boundaries of the edge forming chamber 185 and the boundaries of the central forming chamber 165. The edge lateral baffles 190 can be aligned about flush with the interior facing surface 135 of the shield 130. The edge lateral baffles 190 can be oriented generally orthogonal to the machine direction, as shown in FIG. 2. Embodiments in which the edge lateral baffles 190 are not oriented generally orthogonal to the machine direction of the core pocket 50 are also contemplated. The sheets are sized and dimensioned to fit within the edge forming chamber 185. The edge lateral baffles 190 and central lateral baffles 175 can be formed from sheets of stainless steel, titanium, or other material suitable for use in high speed manufacturing operations.

The central lateral baffles 175 can be spaced apart from one another in the machine direction by about 0.01 to about 0.04 radians. In one embodiment, the central lateral baffles 175 can be spaced apart from one another in the machine direction by about 18 mm. The edge lateral baffles 190 can be spaced apart from one another in the machine direction by about 0.01 to about 0.04 radians. In one embodiment, the edge lateral baffles 190 can be spaced apart from one another in the machine direction by about 18 mm. The edge lateral baffles 190 and central lateral baffles 175 can have a thickness in the MD direction between about 0.5 mm to about 4 mm. The edge lateral baffles 190 and central lateral baffles 175 can have a height in the z direction between about 10 mm and about 40 mm. These dimensions are provided by way of example and not to be limiting, as other dimensions are practical and are a function of the dimensions of the core pocket 50 and materials from which the core pocket 50 is fabricated.

The core pocket 50 can further comprise an edge foraminous forming surface 195 in air-flow communication with the edge forming chamber 185.

The central foraminous forming surface 180 and the edge foraminous forming surface 195 are highly pervious to the flow of air. The central foraminous forming surface 180 and the edge foraminous forming surface 195 can comprise one or more sheets which are permeable to air and have a high percent open area. By way of example, and not to be limiting, the edge foraminous forming surface 195 and central foraminous forming surface 180 can have a percent open area of about 50% percent. The openings in the screen can be about 0.25 mm in diameter. The central foraminous forming surface 180 and the edge foraminous forming surface 195 can be comprised of a thin sheet of stainless steel, titanium, or other material stiff enough to be used in high speed manufacturing operations and have electroetched openings. The central foraminous forming surface 180 and the edge foraminous forming surface 195 can be comprised of stainless steel, titanium, or other material suitable for use in high speed manufacturing operations and have electroetched openings. The central foraminous forming surface 180 and the edge foraminous forming surface 195 can be formed from two or more sheets of foraminous material associated with one another or can be comprised of a single sheet of foraminous material. WO2001042549A1, filed Dec. 8, 2000 and WO2000029656A1, filed Nov. 17, 1999 describe an embodiment of foraminous forming surfaces.

The edge lateral baffles 190 can span the space between the plane defined by the interior facing surface 135 of the shield 130, which can be flat or curved, and the interior facing surface of the edge foraminous forming surface 195. The central lateral baffles 175 can span the space between a plane defined by the interior facing surface 135 of the shield 130 and the interior facing surface of the central foraminous forming surface 180.

The core pocket 50 can optionally comprise a central support mesh 201 adjacent the central foraminous forming surface 180. The core pocket 50 can also optionally comprise an edge support mesh 202 adjacent the edge foraminous forming surface 195. The central support mesh 201 can extend between the central foraminous forming surface 180 and the central lateral baffles 175. The edge support mesh 202 can extend between the edge foraminous forming surface 195 and the edge lateral baffles 190.

The core pocket 50 can optionally comprise a peripheral edge template 350 having a void 355 in the shape of the air-laid fibrous article to be formed. The peripheral edge template 350 can be a separate element attached to the edge forming chamber 185 or can be integral with edge forming chamber 185, such that the edge forming chamber 185 and peripheral edge template 350 are comprised of a unitary material. The peripheral edge template 350 can be positioned adjacent the exterior surface of edge foraminous forming surface 195 in an overlying relationship.

The peripheral edge template 350 can comprise a sheet of material suitable for use in high speed manufacturing operations. The thickness of the peripheral edge template can be selected to correspond with the desired thickness of the air-laid fibrous article 100 in the z direction or a thickness such that the air-laid fibrous article 100 is the proper thickness for further downstream processing. The boundaries of the peripheral edge template 350 can be selected to correspond with the desired shape of the air-laid fibrous article 100 in the MD-CD plane of the air-laid fibrous article 100 or the proper shape for further downstream processing. The term downstream can be understood as the direction of processing from the start of manufacturing the absorbent article towards the end of manufacturing. The term upstream can be understood as the direction in processing opposite downstream.

Figure 3:
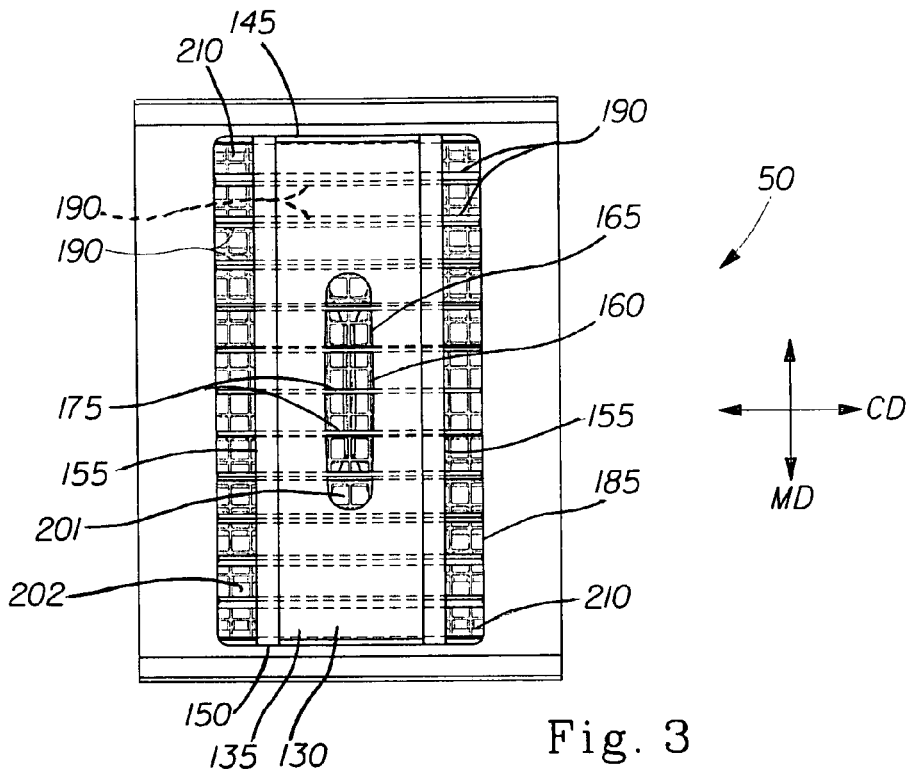
FIG. 3 is a bottom view of a core pocket.

A plan view of one embodiment of core pocket 50 in which the interior facing surface 135 of the shield 130 is presented to the viewer is shown in FIG. 3. As shown in FIG. 3, the core pocket 50 comprises a pair of edge openings 210. The edge openings 210 extend along the shield 130 in the machine direction and extend laterally in the cross direction beyond the shield lateral side edges 155. The edge openings 210 are defined by the spaces between the shield lateral side edges 155 and the edges of the edge forming chamber 185. The edge forming chamber 185 can be in air-flow communication with the edge openings 210. The edge openings 210 can extend from the shield first end 145 to the shield second end 150. The shield 130 can be generally rectangular. Other shapes of the shield 130 are also possible.

By way of example, and not to be limiting, each edge opening 210 can have a width in the cross direction between about 10 mm and about 60 mm.

The core pocket 50 can be configured such that different air pressures can be applied to the central foraminous forming surface 180 and the edge foraminous forming surface 195. Ambient air pressure, positive air pressure, and negative air pressure can be useful in forming air-laid fibrous articles. In describing ambient, positive, and negative air pressures, as used herein, the origin dividing positive pressure and negative pressure is atmospheric pressure (approximately 101.325 kPa), with positive pressures defined as being greater than one atmosphere, ambient pressure being atmospheric pressure, and negative pressures being less than one atmosphere. Particular magnitudes of pressures reported herein are absolute pressures.

In the embodiment shown in FIG. 3, air pressure applied to the central opening 160 can be transmitted through the central opening 160, between the central lateral baffles 175 and into the central forming chamber 165. Air pressure in the central forming chamber 165 can be applied to the central foraminous forming surface 180. If a central support mesh 201 is present, air pressure can be transmitted though the central support mesh 201 to the central foraminous forming surface 180. The wall or walls of the central forming chamber 165 can be made of material impervious to air-flow and joined to one another by seals, seams, welds, or connections that are also impervious to air-flow. Thus, the central forming chamber 165 and edge forming chamber 185 can be isolated from one another in that the air pressure in the central forming chamber 165 can be different than the air pressure in the edge forming chamber 185 and air-flow between the central forming chamber 165 and the edge forming chamber 185 can be small enough to be negligible or even nonexistent. Thus, the edge foraminous forming surface 195 can have a pressure applied thereto that is independent of the pressure applied to the central foraminous forming surface 180 and the pressures applied to the edge foraminous forming surface 195 and the central foraminous forming surface 180 can be independently controlled.

In the embodiment shown in FIG. 3, air pressure applied to the edge openings 210 can be transmitted through the edge openings 210, between the edge lateral baffles 190 into the edge forming chamber 185. With or without the edge lateral baffles, air pressure applied to the edge openings 210 can be transmitted throughout the edge forming chamber 185 such that the pressure applied to the edge openings 210 is also applied to the portions of the edge forming chamber 185 overlying the shield 130. Thus, an "island" of one pressure can be applied to the central foraminous forming surface 180 that is surrounded by a "ring" of another pressure. In effect, pressure applied to the edge forming chamber 185 is bridged across the shield 130.

Air pressure in the edge forming chamber 185 can be applied to the edge foraminous forming surface 195. If edge support mesh 202 is present, air pressure can be transmitted through the edge support mesh 202 to the edge foraminous forming surface 195.

Figure 4:
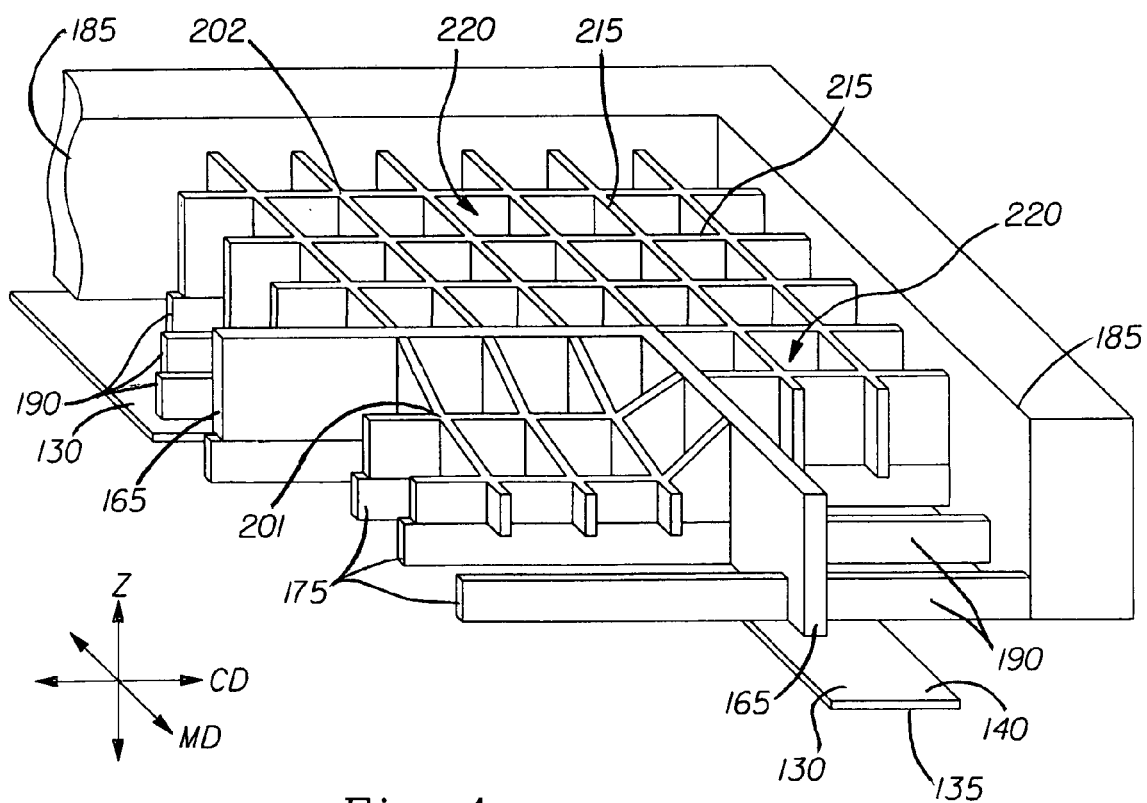
FIG. 4 is a cutaway view of a core pocket with the central support mesh and edge support mesh exposed.

If a central support mesh 201 is present, the central support mesh 201 can be joined to the edges of the central forming chamber 165, as shown in FIG. 4. The central support mesh 201 can provide support to the central foraminous forming surface 180 by distributing load applied to the central foraminous forming surface 180 to the boundaries of the central forming chamber 165 and/or the central lateral baffle 175, which can reduce deformation of the central foraminous forming surface 180. As shown in FIG. 4, the central support mesh 201 can be inset into the central forming chamber 165 such that central support mesh 201 is about flush with the exterior edge of the central forming chamber 165 that is oriented away from the exterior facing surface 140 of shield 130.

Similarly, if edge support mesh 202 is present, the edge support mesh 202 can be joined to the boundaries of the edge forming chamber 185 and the boundaries of the central forming chamber 165. The edge support mesh 202 can provide support to the edge foraminous forming surface 195 in the same manner as the central support mesh 201. The edge support mesh 202 can be inset into the edge forming chamber 185 such that edge support mesh 202 is about flush with the exterior edge of the edge forming chamber 185 that is oriented away from the exterior facing surface 140 of shield 130. In this arrangement, the central forming chamber 165 can be described as projecting through the central support mesh 201 and the edge support mesh 202. In this arrangement, air flow between the central forming chamber 165 and the edge forming chamber 185 can be small enough to be negligible or even non-existent and the air pressure in the central forming chamber 165 can be different from the air pressure in the edge forming chamber 185. Without being bound by theory, it is thought that by delivering different pressures to the edge forming chamber 185 and central forming chamber 165, the amount of scarfing needed to form a fibrous article having one surface that is contoured in the z-direction and another surface that is flat can be reduced.

The central support mesh 201 can extend between the central foraminous forming surface 180 and the central lateral baffles 175 and can be in contact with the central foraminous forming surface 180 and the central lateral baffles 175, if present. In this configuration, the central support mesh 201, which can be a structure having a plurality of open spaces, can fill all the space between the central foraminous forming surface 180 and the central lateral baffles 175 if present.

The edge support mesh 202 can extend between the edge foraminous forming surface 195 and the edge lateral baffles 190 and can be in contact with both the edge foraminous forming surface 195 and the edge lateral baffles 190, if present. In this configuration, the edge support mesh 202, which can be a structure having a plurality of open spaces, can fill all the space between the edge foraminous forming surface 195 and the edge lateral baffles 190 if present.

The central support mesh 201 and edge support mesh 202 can be comprised of stainless steel, titanium, or other material suitable for use in high speed manufacturing operations. Support mesh can be a product described as honeycomb described in WO2001042549A1, filed Dec. 8, 2000, WO2000029656A1, filed Nov. 17, 1999, or WO2001098574A2, filed Jun. 19, 2001. The central support mesh 201 and edge support mesh 202 can have a high percent open area permitting air flow without significant resistance. The central support mesh 201 and edge support mesh 202 can have a plurality of open spaces. The central support mesh 201 and the edge support mesh 202 can be a web of sheet metal comprised of strips of corrugated sheet 4metal joined to one another at the bending axes of the corrugations.

As shown in FIG. 4, central support mesh 201 and edge support mesh 202 can be comprised of mesh walls 215 and mesh cells 220. Portions of the mesh walls 215 can be coordinated to be in alignment with the edges of central lateral baffles 175, thereby substantially preventing movement of air in the machine direction of central forming chamber 165. Portions of the mesh walls 215 can be coordinated to be in alignment with and sealed to the central lateral baffles 175, thereby substantially preventing movement of air in the machine direction of central forming chamber 165.

The edge support mesh 202 can be configured with respect to the edge foraminous forming surface 195 and the edge lateral baffles 190 in the same manner as the central support mesh 201 can be configured with respect to the central foraminous forming surface 180 and the central lateral baffles 175. Portions of the mesh walls 215 can be coordinated to be in alignment with the edges of edge lateral baffles 190, thereby substantially preventing movement of air in the machine direction of edge forming chamber 185. Portions of the mesh walls 215 can be coordinated to be in alignment with and sealed to the edge lateral baffles 190, thereby substantially preventing movement of air in the machine direction of edge forming chamber 185.

The mesh walls of the central support mesh 201 and the edge support mesh 202 need not be in alignment with or sealed to the central lateral baffles 175 and edge lateral baffles 190. In general, small mesh cells 220 can sufficiently resist air flow in the machine direction of the core pocket. By way of example, and not to be limiting, mesh cells 220 having approximately rectangular openings about 13 mm by about 5 mm, in a staggered relationship, such as a running or stretcher bond brick pattern, can be used to sufficiently reduce air flow in the machine direction of the core pocket 50. By way of example, and not to be limiting, the central support mesh 201 and edge support mesh 202 can be comprised of material having a thickness of about 0.2 mm. Without being bound by theory, it is thought that the tortuous pathway for air flow through the spaces between the central support mesh 201 and central lateral baffles 175 and the spaces between the edge support mesh 202 and the edge lateral baffles 190 can offer sufficient resistance to air flow in the machine direction of the core pocket 50.

Figure 5:
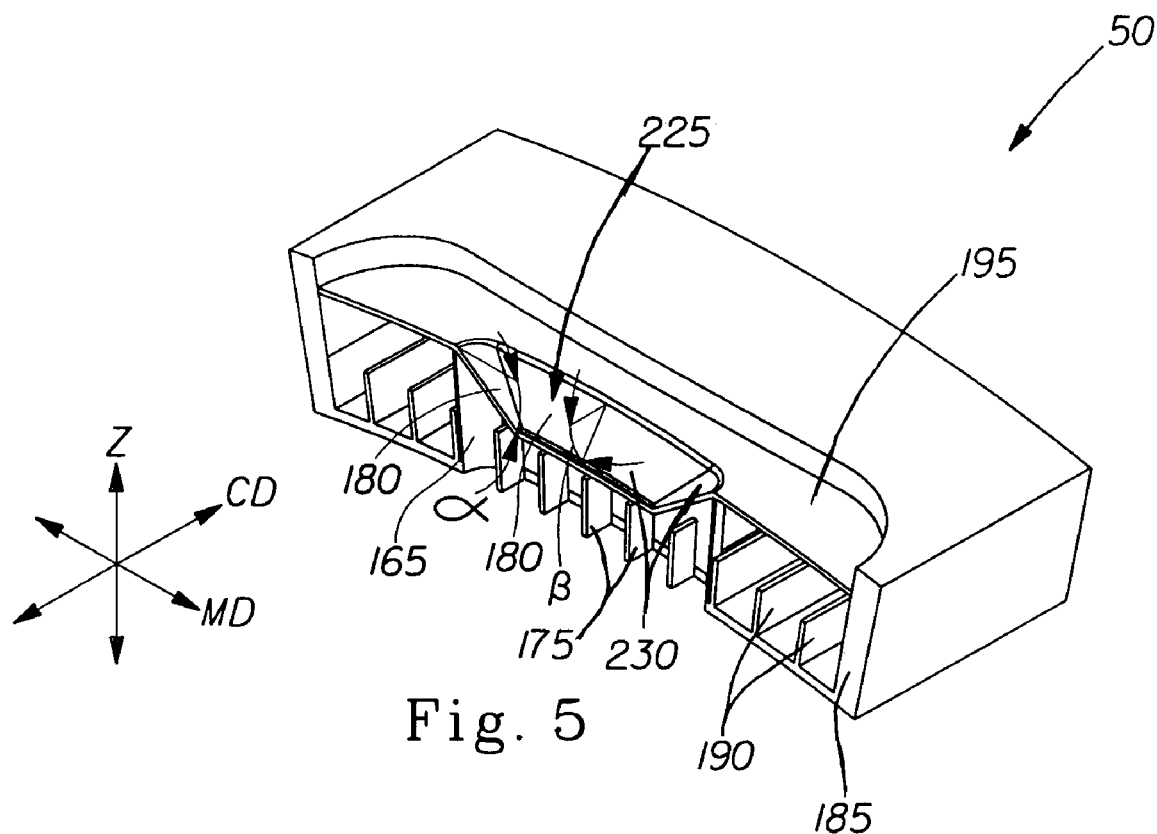
FIG. 5 is a cutaway view of one embodiment of the core pocket, as indicated by Section 5-5.

In one embodiment of the core pocket 50, central foraminous forming surface 180 can have a recessed portion relative to the edge foraminous forming surface 195. Non-limiting examples for the shape of the recess can include a frustum, a frustum having an oval shaped base, a frustum having an irregularly shaped base and top, and a pyramidal frustum. As shown in FIG. 5, the central foraminous forming surface 180 and edge foraminous forming surface 195 can be considered to a have a machine direction MD and a cross direction CD. The recessed portion 225 can be generally characterized by the angles formed by the recess in the machine direction and cross direction. The angle of the recess in the machine direction α can be between about 0° and about 90°, with 0° corresponding to an arrangement in which the central foraminous forming surface 180 is not recessed relative to the edge foraminous forming surface 195. The angle of the recess in the machine direction α can be between about 1° and about 45°. The angle of the recess in the cross direction β can be between about 0° and about 90°, with 0° corresponding to an arrangement in which the central foraminous forming surface 180 is not recessed relative to the edge foraminous forming surface 195. The angle of the recess in the cross direction β can be between about 1° and about 70°. The specific ranges for angles α and β are provided by way of example and not to be limiting. The angles α and β can be the same or different and the angle on one side of the recess can be different from the angle on the opposing side. The recess walls 230 can be straight or curved, combinations of straight sections, combinations of curved sections, or combinations of straight and curved sections. The configurations for the recessed portion 225 described herein are by way of example only and not to be limiting as other configurations are possible. The central foraminous forming surface 180 and the edge foraminous forming surface 195 can be in plane with one another so as to be considered flat with respect to one another.

Figure 6:
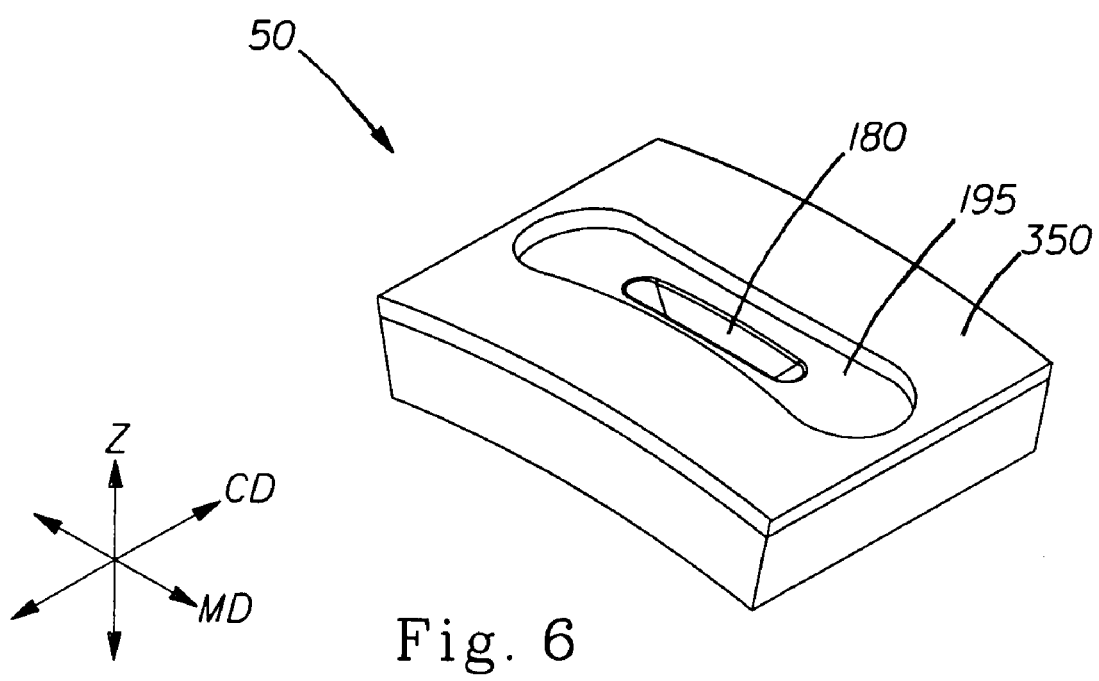
FIG. 6 is a perspective view of one embodiment of the core pocket.

By way of example, and not to be limiting, the edge foraminous forming surface 195 and the central foraminous forming surface 180, upon which fibers are deposited, can have the shape of a core of a sanitary napkin, diaper, incontinent pad, or other absorbent article designed to be worn in the crotch of the wearer. A perspective cut-away view illustrating an edge foraminous forming surface 195 and a central foraminous forming surface 180, upon which fibers are deposited, having the shape of a core for sanitary napkin is shown in FIG. 5. To provide for a well defined periphery and thickness of the air-laid fibrous article 100, the central foraminous forming surface 180 and the edge foraminous forming surface 195 can be recessed relative to the boundaries of the edge forming chamber 185, as shown in FIG. 5, or recessed relative to a peripheral edge template 350, as shown in FIG. 6.

As discussed previously, the core pocket 50 can optionally comprise a peripheral edge template 350 that can provide for a well defined periphery and thickness of the air-laid fibrous article 100. By overlaying a peripheral edge template 350 over the foraminous forming surfaces, the foraminous forming surfaces can be recessed relative to the exterior facing surface of the core pocket 50 which is the side of the core pocket 50 oriented away from the shield 130.

By way of example, and not to be limiting, the peripheral edge template 350 can have the shape of a core of a sanitary napkin, diaper, incontinent pad, or other absorbent article designed to be worn in the crotch of the wearer.

Figure 7:
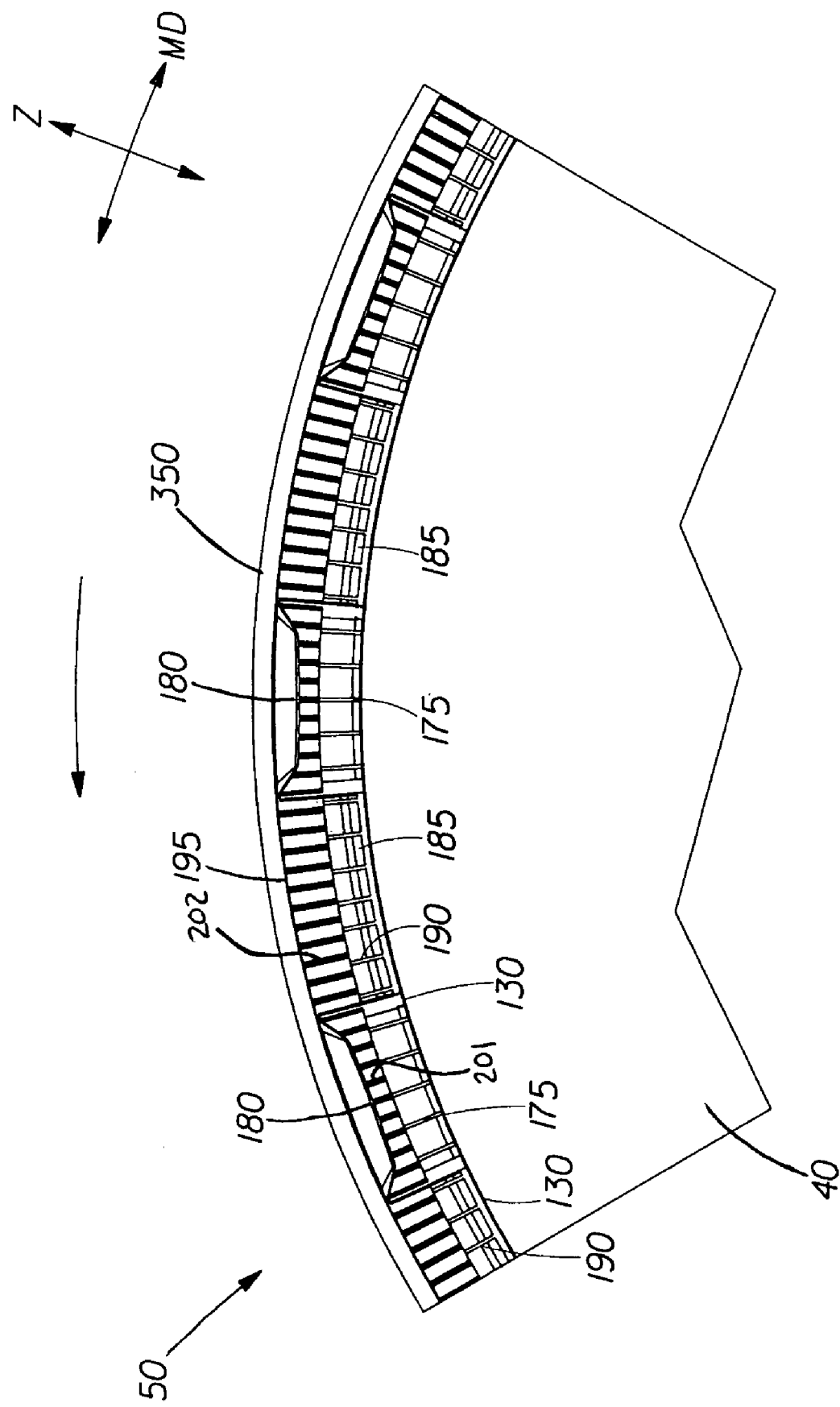
FIG. 7 is a cross sectional view of a core pocket comprising a plurality of central forming chambers in an edge forming chamber, the core pocket being mounted on a deposition drum (viewed from the opposite side as the view provided in FIG. 1).

The core pocket 50 can comprise one or more central forming chambers 165 disposed in a single edge forming chamber 185, as shown in FIG. 7. FIG. 7 is a cross sectional view of a core pocket 50 mounted on deposition drum 40 as viewed from the opposite side as the view provided in FIG. 1. In the embodiment shown in FIG. 7, the core pocket 50 has a plurality of central forming chambers 165 within a single edge forming chamber 185. In this configuration, a web of air-laid fibrous material in which a plurality of zones of material deposited above the central forming chambers can be formed with the apparatus 10. A single edge forming chamber 185 can extend circumferentially about deposition drum 40.

In apparatus 10, in which the core pockets 50 are disposed in a circumferential relationship about the periphery of deposition drum 40, all of the components of the core pocket 50 can have an arcuate shape in the machine direction. By way of example, and not to be limiting, a core pocket 50 having an arcuate shape in the machine direction can have a length as measured in the machine direction between about 0.15 and about 0.55 radians. By way of example, and not to be limiting, the central opening 160 for a core pocket 50 having an arcuate shape in the machine direction can have a length as measured in the machine direction between about 0.1 and about 0.4 radians.

In apparatus 10 in which the core pockets are not disposed about the periphery of a deposition drum 40 but travel in a flat plane as air-laid fibrous articles 100 are formed, the core pocket 50, and the components thereof, can have a flat shape in the machine direction.

An embodiment of apparatus 10 further comprising an air-distribution manifold 60 operatively related to the core pocket 50 is shown in FIG. 1. By operatively related it is meant that the air-distribution manifold 60 is positioned such that the core pocket 50 can slide along the air-distribution manifold 60. In one embodiment, the air-distribution manifold 60 can have a curved air-distribution surface. Air-distribution manifold 60 can be stationary. In the embodiment shown in FIG. 1, the core pocket 50 can slide along the air-distribution manifold 60 as the deposition drum 40 rotates. In this embodiment, the core pocket 50 can be disposed in a circumferential relationship about the periphery of deposition drum 40. The shield 130, central forming chamber 165, and edge forming chamber 185 can have an arcuate shape in the machine direction that generally conforms to the curved peripheral surface of the air-distribution manifold 60. The radius of curvature of the shield 130, central forming chamber 165, and edge forming chamber 185 can be about the same or slightly greater than the curvature of the air-distribution surface of the air-distribution manifold 60. Furthermore, by operatively related, it is meant that the air-distribution manifold 60 can be in air-flow communication with one or more core pockets 50 as the deposition drum 40 rotates about the air-distribution manifold 60 such that controlled magnitudes of air pressure can be applied to portions of the core pocket 50. For example, the air pressure applied by the air-distribution manifold 60 to the central forming chamber 165 can differ from the air pressure applied to the edge forming chamber 185.

Figure 8:
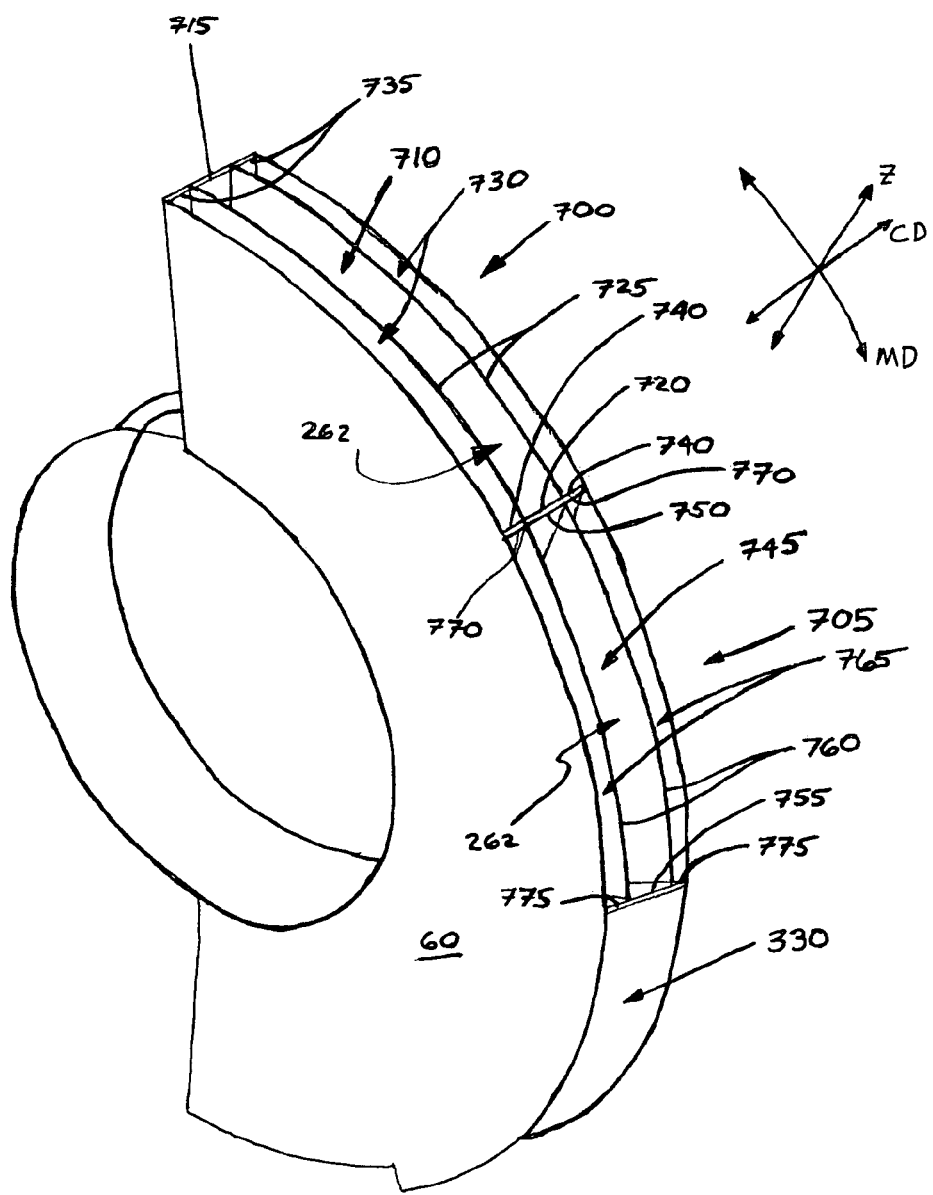
FIG. 8 is a perspective view of one embodiment of an air-distribution manifold.

In one embodiment, as shown in FIG. 8, the air-distribution manifold 60 can comprise a first forming area 700 and a second forming area 705. The first forming area 700 can comprise a first central zone 710. The first central zone 710 can have a first central zone first end 715, a first central zone second end 720 opposing the first central zone first end 715, and a pair of opposing first central zone lateral side edges 725 extending from the first central zone first end 715 to the first central zone second end 720. The first central zone second end 720 can be adjacent the second central zone first end 750.

The air-distribution manifold 60 can further comprise a pair of first edge zones 730. Each first edge zone 730 can be adjacent a first central zone lateral side edge 725.

In describing the first central zone 710 as having a first central zone first end 715, the first central zone first end 715 is the end of the first central zone 710 which the core pocket 50 first encounters as the core pocket 50 reaches the location in the apparatus 10 where air-entrained fibers are directed towards the core pocket 50. The first central zone second end 720 is the end of the first central zone 710 which the core pocket 50 encounters as the core pocket 50 slides along the air-distribution manifold 60 after the core pocket 50 has passed the first central zone first end 715.

The first central zone 710 and the first edge zones 730 are not in air-flow communication with one another as the core pocket 50 slides along the zones of the air-distribution manifold 60. That is, the air pressure in the first central zone 710 can be maintained at a pressure that differs from the air pressure in the first edge zones 730 and the air-flow between the first central zone 710 and the first edge zones 730 can be small enough to be to be negligible or even nonexistent. To reduce the amount of air-flow between the first central zone 710 and the first edge zones 730 when the core pocket 50 is overlying these zones, a sealing material, such as felt, can be affixed along the boundaries between the first central zone 710 and the first edge zones 730 along the peripheral surface of the air-distribution manifold 60. To further reduce the amount of air-flow between the first central zone 710 and the first edge zones 730 when the core pocket 50 is overlying these zones, a sealing material, such as Multifill Bearing Tape having a width of about 1 cm and a thickness of about 0.8 mm supplied by Garlock Bearings, LLC, can be affixed to the interior facing surface 135 of the shield 130 such that the sealing material is approximately coincident with the boundaries between the first central zone 710 and the first edge zones 730 of the air-distribution manifold 60 and aligned in the machine direction of the core pocket 50.

As shown in FIG. 8, each first edge zone 730 can have a first edge zone first end 735. The first edge zone first end 735 can be aligned with the first central zone first end 715. The first edge zone first end 735 does not have to be aligned with the first central zone first end 715. Each first edge zone 730 can further have a first edge zone second end 740 opposing the first edge zone first end 735. The first edge zone second end 740 can be aligned with the first central zone second end 720. The first edge zone second end 740 does not have to be aligned with the first central zone second end 720. Furthermore, the first edge zones 730 need not have the same geometry as one another.

The first forming area 700 of the air-distribution manifold 60 is located in operative relationship with the first discharge chute 30 that distributes first fibers 12 in the first forming region 1. That is, the first forming region 1 is the concurrence of the first discharge chute 30, the first forming area 700 of the air-distribution manifold, and a core pocket 50 passing there between.

As shown in FIG. 8, the air-distribution manifold can also comprise a second central zone 745. The second central zone 745 can have a second central zone first end 750, a second central zone second end 755 opposing the second central zone first end 750, and a pair of opposing second central zone lateral side edges 760 extending from the second central zone first end 750 to the second central zone second end 755, wherein the second central zone first end 750 is adjacent the first central zone second end 720. The air-distribution manifold can further comprise a pair of second edge zones 765, each of the second edge zones 765 adjacent a second central zone lateral side edge 760.

As shown in FIG. 8, each second edge zone 765 can have a second edge zone first end 770. The second edge zone first end 770 can be aligned with the second central zone first end 750. The second edge zone first end 770 does not have to be aligned with the second central zone first end 750. Each second edge zone 765 can further have a second edge zone second end 775 opposing the second edge zone first end 770. The second edge zone second end 775 can be aligned with the second central zone second end 755. The second edge zone second end 775 does not have to be aligned with the second central zone second end 755. Furthermore, the second edge zones 765 need not have the same geometry as one another.

The air-distribution manifold 60 can also comprise a hold down zone 330. The hold down zone 330 can be disposed adjacent the second central zone second end 755. The pressure applied at the hold down zone 330 can be about 4 kPa. The pressure applied at the hold down zone 330 can be between about 1 kPa and about 10 kPa. These pressures are provided by way of example and not to be limiting.

The first central zone 710 has a first central zone width in the cross direction defined by the shortest distance between the first central zone lateral side edges 725. The first central zone width can be between about 15 mm and about 50 mm. The first central zone 710 can have a width of about 31 mm. The length of the first central zone 710, as measured in the machine direction can be about 195 mm. Each first edge zone 730 also has a first edge zone width in the cross direction. The first edge zone width can be between about 5 mm and about 40 mm.

The second central zone 745 has a second central zone width in the cross direction defined by the shortest distance between the second central zone lateral side edges 760. The second central zone width can be the same as the first central zone width. Each second edge zone 765 also has a second edge zone width in the cross direction. The second edge zone width can be the same as the first edge zone width.

The hold down zone 330 has a hold down zone width in the cross direction. The hold down zone width can be between about 25 mm and about 130 mm. The hold down zone width can be about 60 mm. The hold down zone width can be about the same as the sum of the second central zone width and each second edge zone width. The length of the hold down zone, as measured in the machine direction, can be about 104.5 mm. The first central zone width, second central zone width, first edge zone width, second edge zone width, hold down zone length, and hold down zone width provided herein are by way of example and not to be limiting given that these dimensions are ultimately governed by the desired geometry of air-laid fibrous article 100, the dimensions of the core pocket 50, and the geometry of the air-distribution manifold 60. For an air-distribution manifold 60 having a curved air-distribution surface 262, the lengths reported are lengths about the circumference of the air-distribution manifold 60.

As with the boundaries between the first central zone 710 and first edge zones 730, sealing materials can be applied between the boundaries of the different zones of the air-distribution manifold 60. For instance, sealing materials can be applied between the second central zone 745 and the second edge zones 765, between the second central zone 745 and the first central zone 710, between the second edge zones 765 and the first edge zones 730, between the hold down zone 330 and the second central zone 745, and between the hold down zone 330 and the second edge zones 765.

The first central zone 710 can be in air-flow communication with a source of air pressure. The air pressure in the first central zone 710 can be negative. Some people skilled in the art refer to negative pressure as vacuum or vacuum pressure. Similarly, each first edge zone 730 can be in air-flow communication with a source of air pressure. The air-distribution manifold 60 can be operatively related to one or more core pockets 50 such that as a core pocket 50 slides along the air-distribution manifold 60, the first central zone 710 of the air-distribution manifold 60 can be in air-flow communication with the central opening 160 in the shield 130. Furthermore, the air-distribution manifold 60 can be operatively related to one or more core pockets 50 such that as the core pocket 50 slides along the air-distribution manifold 60, the first edge zones 730 can be in air-flow communication with the edge openings 210 of the core pocket 50.

One way to configure the air-distribution manifold 60 to form an air-laid fibrous article comprised of an island of a first fibrous material surrounded in plane (the MD-CD plane) by a second fibrous material is as follows. The pressure in the first central zone 710 can be negative. The pressure in the first edge zones 730 can be positive, ambient, or negative but greater than the pressure in the first central zone 710. In this configuration, a stream of loose air-entrained first fibers 12 can be provided. The core pocket 50 can be provided in operative relationship with the stream of loose air-entrained first fibers 12. In this configuration, first fibers 12 are drawn to the central foraminous forming surface 180 of the core pocket 50. Positive pressure in the first edge zones 730 substantially prevents first fibers 12 from being deposited on the edge foraminous forming surface 195. Without being bound by theory, it is believed that positive pressure from the first edge zones 730, which is transported through the core pocket 50 to the edge foraminous forming surface 195, can act as a barrier to deposition of first fibers 12. First fibers 12 that do impinge upon the edge foraminous forming surface 195 may be dislodged and re-suspended by the positive pressure in the first edge zones 730 and subsequently deposited on the central foraminous forming surface 180. If the pressure on the first edge zones 730 is ambient or negative but greater than the pressure in the first central zone 710, air can be drawn from the edge forming chamber 185 to assist in directing first fibers 12 towards the central foraminous forming surface 180 and/or substantially reduce the amount of first fibers 12 deposited on the edge foraminous forming surface 195. In this configuration, as the core pocket exits the first forming region 1, an island of first fibers 12 is deposited on the central foraminous forming surface 180 and the edge foraminous forming surface 195 is substantially free of first fibers 12.

The pressure in the second central zone 745 can be negative to assist in holding down the island of first fibers 12 on the central foraminous forming surface 180. The pressure in the second edge zones 765 can be negative. In this configuration, as the core pocket 50 moves through the second forming region 2 in which a stream of second fibers 612 is provided, second fibers 612 can be deposited in the core pocket 50, the second fibers 612 discharged from the second discharge chute 630 are drawn to the edge foraminous forming surface 195. The pressure in the second central zone 745 should not be so low that second fibers 612 are drawn to be deposited on top of the island of first fibers 12 on the central foraminous forming surface 180. Rather, negative pressure in the second central zone 745, if pressure is applied, should only be of sufficient magnitude to maintain the integrity of the island of first fibers 12 deposited on the central foraminous forming surface 180. Stated in other words, the pressure in the second edge zones 765 can be negative and less than the pressure in the second central zone 745.

Another way to configure the air-distribution manifold 60 to form an air-laid fibrous article comprised of an island of a first fibrous material surrounded in plane (the MD-CD plane) by a second fibrous is as follows. The pressure in the first central zone 710 can be positive, ambient, or negative but greater than the pressure in the first edge zones 730. The pressure in the first edge zones 730 can be negative. In this configuration, a stream of loose air-entrained first fibers 12 can be provided. The core pocket 50 can be provided in operative relationship with the stream of loose air-entrained first fibers 12. In this configuration, first fibers 12 are drawn to the edge foraminous forming surface 195 of the core pocket 50. The positive pressure in the first central zone 710 substantially prevents first fibers 12 from being deposited on the central foraminous forming surface 180. Without being bound by theory, it is believed that the positive pressure from the first central zone 710, which is transported through the core pocket 50 to the central foraminous forming surface 180, acts as a barrier to deposition of first fibers 12. First fibers 12 that do impinge upon the central foraminous forming surface 180 may be dislodged and re-suspended and subsequently deposited on the edge foraminous forming surface 195. If the pressure on the first central zone 710 is ambient or negative but greater than the pressure in the first edge zones 730, air can be drawn from the central forming chamber 165 to assist in directing first fibers 12 towards the edge foraminous forming surface 195 and/or substantially reduce the amount of first fibers 12 deposited on the central foraminous forming surface 180. In this configuration, as the core pocket exits the first forming region 1, a ring of first fibers 12 is deposited on the edge foraminous forming surface 195 and the central foraminous forming surface 180 is substantially free of first fibers 12.

The pressure in the second central zone 745 can be negative. The pressure in the second edge zones 765 can be negative to assist in holding down the ring of first fibers 12 on the edge foraminous forming surface 195. In this configuration, as the core pocket 50 moves through the second forming region 2 in which a stream of second fibers 612 is provided, second fibers 612 can be deposited in the core pocket 50. The second fibers 612 discharged from the second discharge chute 630 can be drawn to the central foraminous forming surface 180. The pressure in the second edge zones 765 should not be so low that second fibers 612 are drawn to be deposited on top of the ring of first fibers 12 on the edge foraminous forming surface 195. Rather, negative pressure in the second edge zones 765, if negative pressure is present, should only be of sufficient magnitude to maintain the integrity of the ring of first fibers 12 deposited on the edge foraminous forming surface 195. Stated in other words, the pressure in the second central zone 745 can be negative and less than the pressure in the second edge zones 765.

The first central zone 710, first edge zones 730, second central zone 745, second edge zones 765, and hold down zone 330 can each be in air-flow communication with a source of air pressure specific to each particular zone. The source of air pressure for each zone can be positive or negative, depending on the configuration of the apparatus 10.

The air-distribution manifold 60 can be operatively related to one or more core pockets 50 such that as a core pocket 50 slides along the air-distribution manifold 60, the first central zone 710 of the air-distribution manifold 60 can be in air-flow communication with the central opening 160 in the shield 130. Furthermore, the air-distribution manifold 60 can be operatively related to one or more core pockets 50 such that as the core pocket 50 slides along the air-distribution manifold 60, the first edge zones 730 can be in air-flow communication with the edge openings 210 of the core pocket 50.

Pressures in the range of about 6.7 kPa and about 16 kPa may be appropriate for drawing fibers to particular portions of the core pocket. Pressures in the range of about 2 kPa and about 20 kPa may be appropriate for drawing fibers to particular portions of the core pocket. These pressures stated are by way of example only and are not to be limiting, as other pressures can be applied with the result that air-laid fibrous articles having different properties can be formed. Pressures greater than one atmosphere may be appropriate for preventing fibers from being deposited on a foraminous forming screen. Pressures between about 101.325 kPa and about 120 kPa may be appropriate for preventing fibers from being deposited on a foraminous forming surface. Pressures between about 101.325 kPa and about 200 kPa may be appropriate for preventing fibers from being deposited on a foraminous forming surface.

The air-distribution manifold 60 illustrated in FIG. 8 has a curved air-distribution surface 262. The air-distribution surface 262 is the portion of the air-distribution manifold 60 facing the core pocket 50 as the core pocket 50 slides over the air-distribution manifold 60. The shield 130, central forming chamber 165, and edge forming chamber 185 can have an arcuate shape in the machine direction that generally conforms to the air-distribution surface 262. The air-distribution manifold 60 can have a flat air-distribution surface 262.

For an air-distribution manifold 60 having a curved air-distribution surface 262, the first central zone 710 can extend between about 0.5 radians and about 0.7 radians. The first edge zones 730 can also extend between about 0.5 radians and about 0.7 radians. The second central zone 745 can extend between about 0.5 radians and about 0.7 radians. The second edge zones 765 can also extend between about 0.5 radians and about 0.7 radians. The hold down zone 330, if present, can extend between about 0.5 radians and about 0.8 radians. The dimensions for the first central zone 710, first edge zones 730, second central zone 745, second edge zones 765, and hold down zone 330 are provided by way of example and not to be limiting. Other dimensions for the first central zone 710, first edge zones 730, second central zone 745, second edge zones 765, and hold down zone 330 are possible and the dimensions are a function of the geometry of the fibrous articles 100, air-distribution manifold 60, and core pocket 50.

Figure 9:
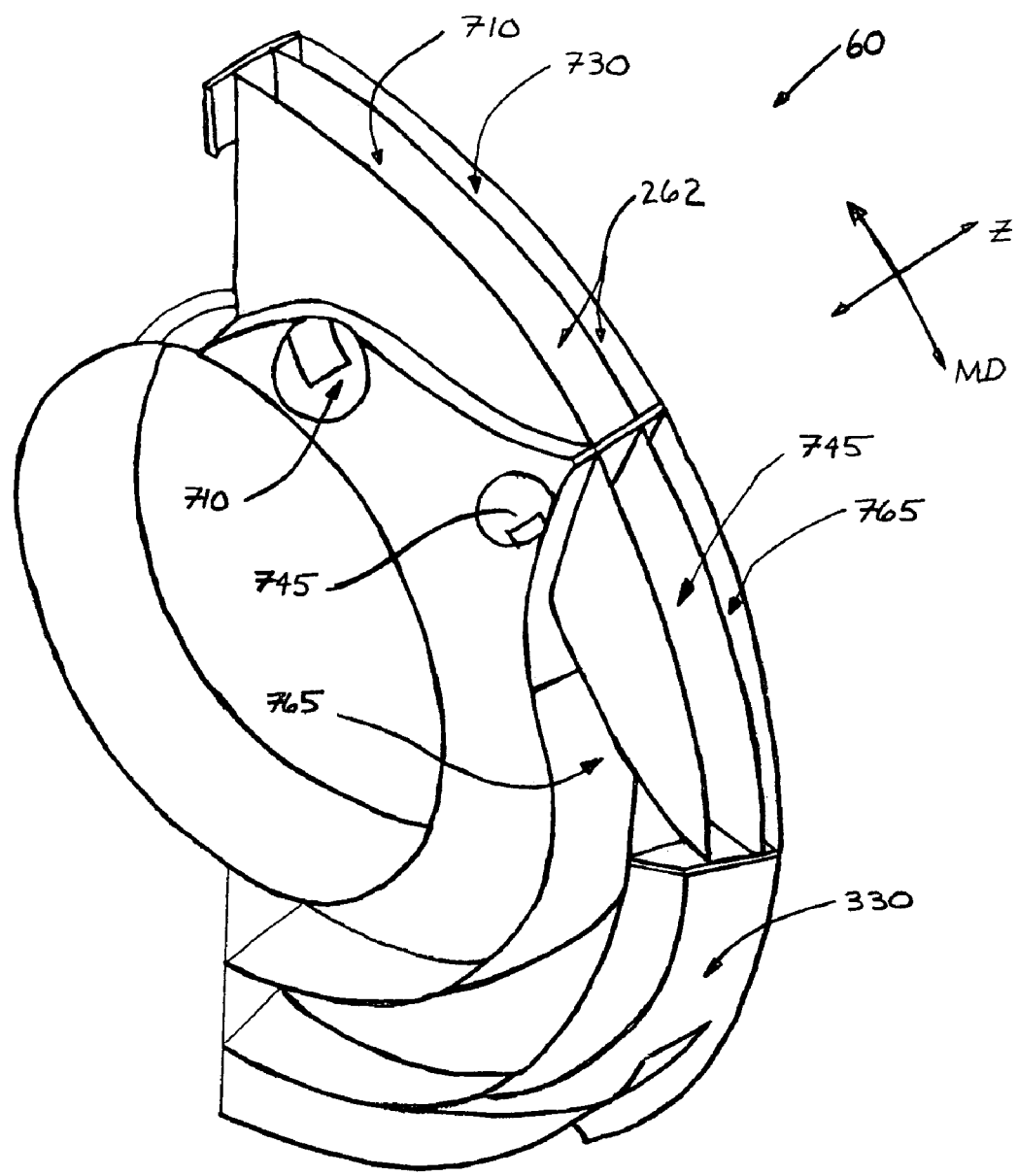
FIG. 9 is a cutaway view of one embodiment of an air-distribution manifold.

A cutaway view of one embodiment of the air-distribution manifold 60 is shown in FIG. 9. As shown in FIG. 9, air pressure can be conducted or conveyed through ducts within the air-distribution manifold 60 to various portions of the air-distribution surface 262. As known by those skilled in the art, there are many possible designs that are suitable for conducting pressures to different portions of an air-distribution manifold.

In one embodiment of apparatus 10 in which the air-distribution manifold 60 has a curved air-distribution surface 262, the core pocket 50 can slide along the air-distribution manifold at an angular velocity of between about 2 radians per second and about 10 radians per second. The core pocket 50 can slide along the air-distribution manifold at an angular velocity of about 7.2 radians per second. The range and particular values for angular velocity for the core pocket 50 are provided by way of example and not to be limiting as other values for the angular velocity of the core pocket 50 are possible.

Figure 10:
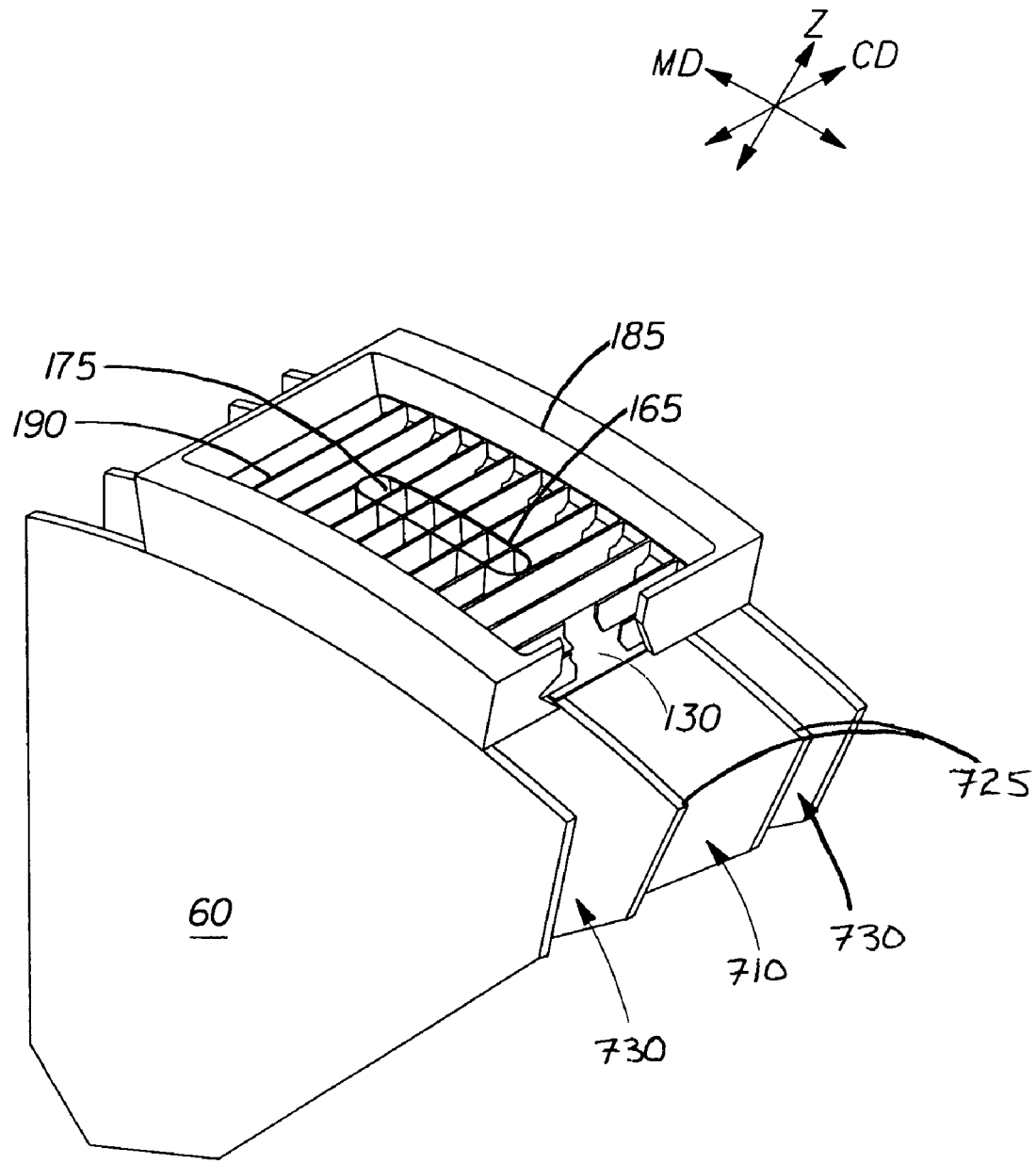
FIG. 10 is schematic of how components of the core pocket can be operatively related to the air-distribution manifold.

An illustration of one embodiment in which the air-distribution manifold 60 is in operative relationship with a portion of a core pocket 50 is shown in FIG. 10. The first central zone 710, shield 130, and central opening 160 are sized and dimensioned so that air pressure in the first central zone 710 can be transmitted to the central forming chamber 165, but not to the edge forming chamber 185. Similarly, each first edge zone 730 of the air-distribution manifold 60 can be in air-flow communication with each edge opening 210 and thereby the edge forming chamber 185. Each first edge zone 730 and each edge opening 210 is sized and dimensioned so that air pressure in the first edge zones 730 is transmitted to the edge forming chamber 185, but not to the central forming chamber 165. By operatively relating the core pocket 50 and air-distribution manifold in this manner, the pressure applied to the central foraminous forming surface 180 can be independently controlled and differ from the pressure applied to the edge foraminous forming surface 195.

Central lateral baffles 175 can also be in slideable and sealable engagement with first central zone 710 and second central zone 745. The central lateral baffles 175 divide the central forming chamber 165 into a plurality of central forming chamber lateral sections that are not in free air-flow communication with one another. Thus, the central lateral baffles 175 substantially reduce or prevent the movement of air in the machine direction through the central forming chamber 165.

Similarly, the edge lateral baffles 190 can be in slideable and sealable engagement with the first edge zones 730 and the second edge zones 765. The edge lateral baffles 190 divide the edge forming chamber 185 into a plurality of edge forming chamber lateral sections that are not in free air-flow communication with one another. By this structure, movement of air in the machine direction through the edge forming chamber 185 can be substantially reduced or prevented.

Reducing movement of air in the machine direction of the core pocket may be desired because as the core pocket 50 slides along the air-distribution manifold 60, different portions of the core pocket 50 may be in air-flow communication with different zones of the air-distribution manifold 60. For instance, as the core pocket 50 moves in the machine direction during formation of the core, when the core pocket 50 is at a particular location, half of the edge openings 210 may be in air-flow communication with the first edge zones 730 and the other half of the edge openings 210 may be in air-flow communication with the second edge zones 765. Without the edge lateral baffles 190, the air pressure acting on the edge forming chamber 185 would be approximately the resultant of the air pressures applied at the first edge zones 730 and the second edge zones 765. This would result in variations of the air pressure applied to portions of the edge foraminous forming surface 195 not corresponding to the location of the different portions of the edge foraminous forming surface 195 relative to the zones on an air-distribution manifold 60 comprising multiple zones. The net result on an air-laid fibrous web could be a gradual variation in the basis weight of the fibrous web in the machine direction and uncontrolled deposition of fibers, which may be undesirable. Central lateral baffles 175 can perform in the same manner.

Figure 11:
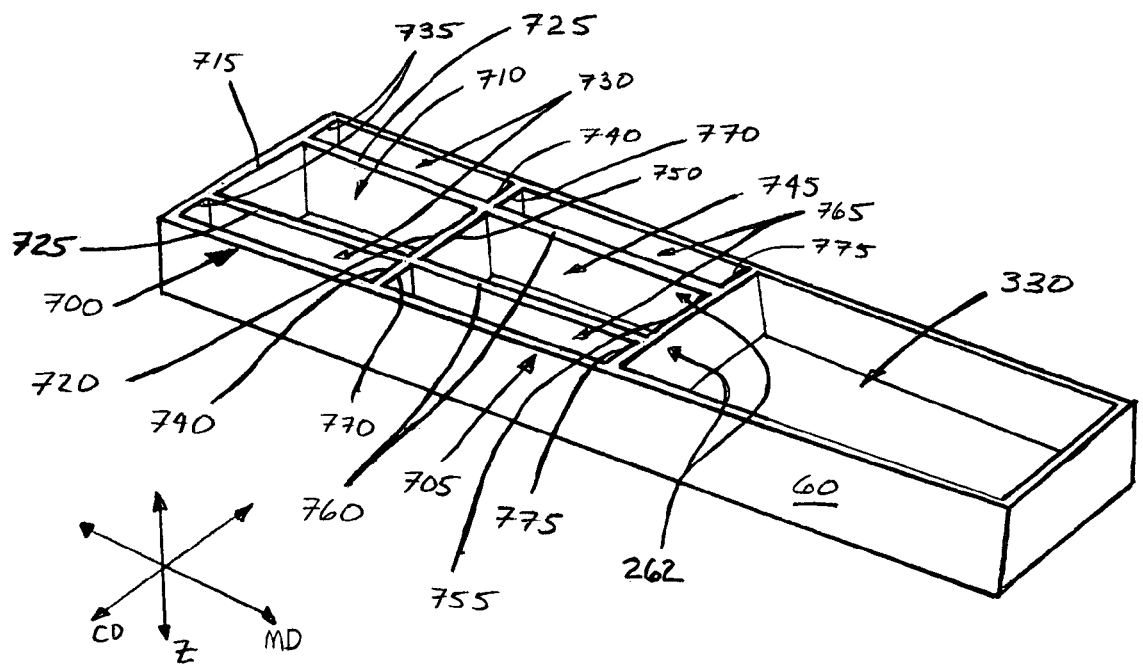
FIG. 11 is a schematic of an embodiment of the air-distribution manifold in which the air-distribution surface is flat.

An embodiment of an air-distribution manifold 60 having a flat air-distribution surface 262 is shown in FIG. 11. For an air-distribution manifold 60, having a flat air-distribution surface 262, the shield 130, central forming chamber 165, and edge forming chamber 185 also can have a flat shape that generally conforms to the flat air-distribution surface 262. An approach to operatively relating a core pocket to a flat air-distribution manifold is illustrated in U.S. Pat. No. 3,973,291 issued to Kolbach, Aug. 10, 1976.

The apparatus 10 can further comprise a scarfing roll 80 positioned in operative relationship with the core pocket 50. The scarfing roll 80 can be positioned so that as the core pocket 50 slides along the air-distribution manifold 60 excess fibrous material deposited on the central foraminous forming surface 180 or the edge foraminous forming surface 195 can be scraped away. If excess fibrous material is deposited on the central foraminous forming surface 180 or the edge foraminous forming surface 195, the scarfing roll 80 contacts the outwardly facing free surface of the fibrous article 100. The scarfing roll 80 can be positioned such that scarfing roll 80 can contact the outwardly facing free surface of the fibrous article 100 without contacting the core pocket 50.

Scarfing roll 80 can be a roll of blades rotating about a shaft, as is known in the art. The movement of the peripheral surface of scarfing roll 80 can remove uneven portions from the free surface of the air-laid fibrous article 100 to produce a more uniform and level surface. The surface of the scarfing roll 80 can be adjusted to provide a desired contour along the scarfed surface of the fibrous article. The scarfing roll 80 can be disposed in a spaced adjacent relationship to the central foraminous forming surface 180 and the edge foraminous forming surface 195 as these surfaces move past the scarfing roll 80.

Scarfing roll 80 can rotate in a direction such that the peripheral surface of the scarfing roll 80 moves counter to the direction the fibrous article 100 moves by the scarfing roll 80.

The process of forming an air-laid fibrous article can be thought of in terms of applying a series of pressures to different portions of the core pocket as the air-laid fibrous article is formed. The pressure applied at the first central zone 710 can be thought of as a first pressure. The pressure applied at the first edge zones 730 can be thought of as a second pressure. The pressure applied at the second edge zones 765 can be thought of as a third pressure. The pressure applied at the second central zone 745 can be thought of as a fourth pressure. The pressure applied at the hold down zone 330 can be thought of as a fifth pressure.

Apparatus 10 can further comprise a forming zone shield 370. Forming zone shields 370 can be configured such that as the core pocket 50 moves through the first forming region 1 and the second forming region 2, the amount of air flow into the core pocket 50 from the surrounding environment is negligible. In other words, the core pocket 50 can be described as being in slideable and sealable engagement with the forming zone shields 370. The forming zone shields 370 can be comprised of any material that that is impervious to air-flow and is suitable for use in high speed manufacturing operations. The seal between the forming zone shields 370 and the core pocket 50 can be comprised of horse hair fiber and felt. The seal between the forming zone shields 370 and core pocket 50 need not completely separate the core pocket 50 from the surrounding environment. Rather, the core pocket 50 can be separated from the surrounding environment in a manner sufficient to prevent unacceptable contamination of the air-laid fibrous article 100 from occurring during formation and to permit sufficient control of air pressures applied to different portions of the core pocket 50 by the air-distribution manifold 60.

Figure 12:
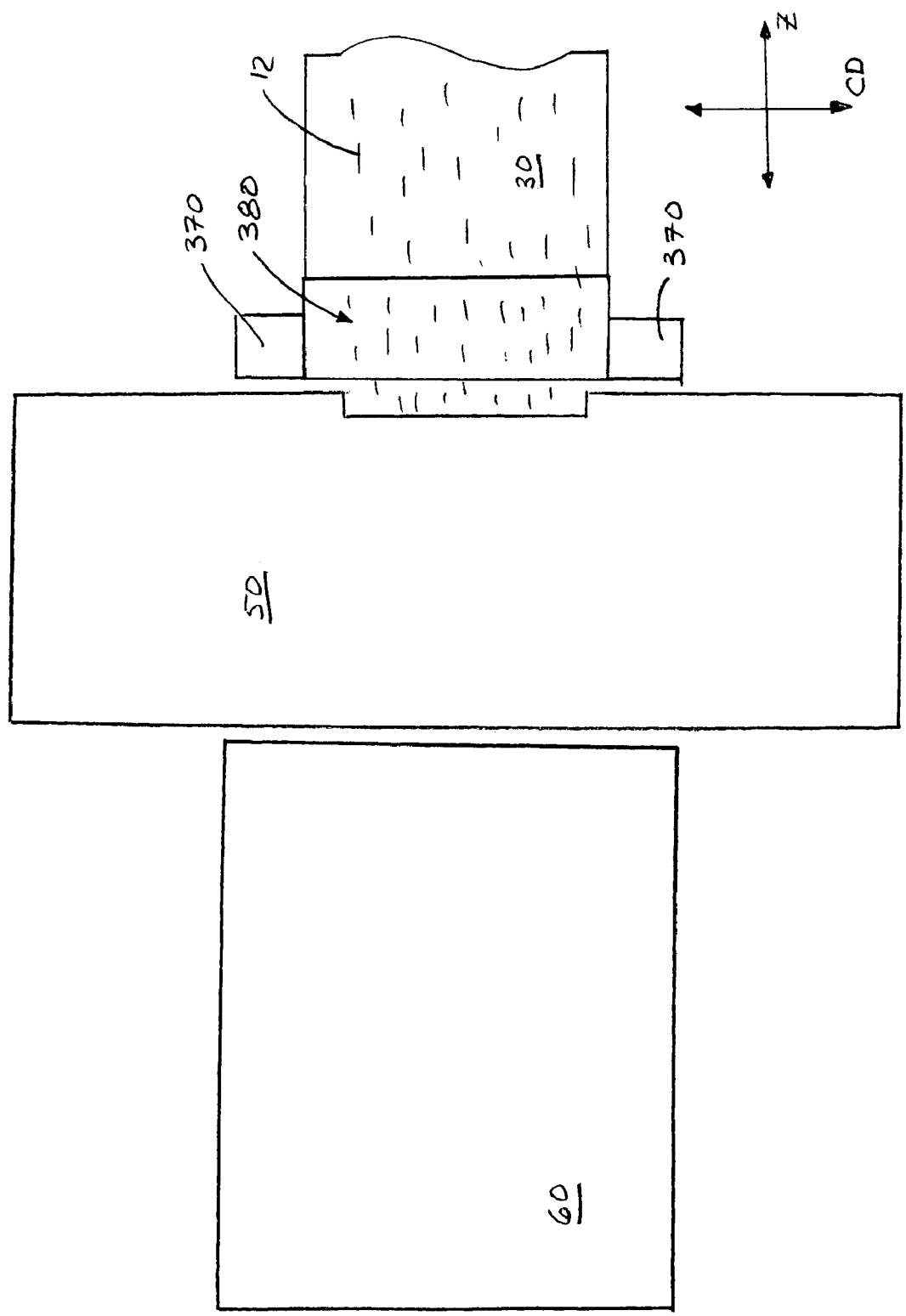
FIG. 12 is a cross sectional view of FIG. 1 looking upstream in the machine direction, as indicated by Section 12-12.

FIG. 12 illustrates a cross section, as marked in FIG. 1, in which the operative relationship between the forming zone shield 370, core pocket 50, and air-distribution manifold 60 are shown. As shown in FIG. 12 the forming zone shield 370 can be positioned to be in slideable and sealable relationship with the core pocket 50.

The first drylap web 8 and second drylap web 608 can be webs of cellulosic material such as wood pulp or other natural or synthetic fibers. In describing the fibers as being air-entrained, other gaseous mediums are also understood to be suitable.

Figure 13:
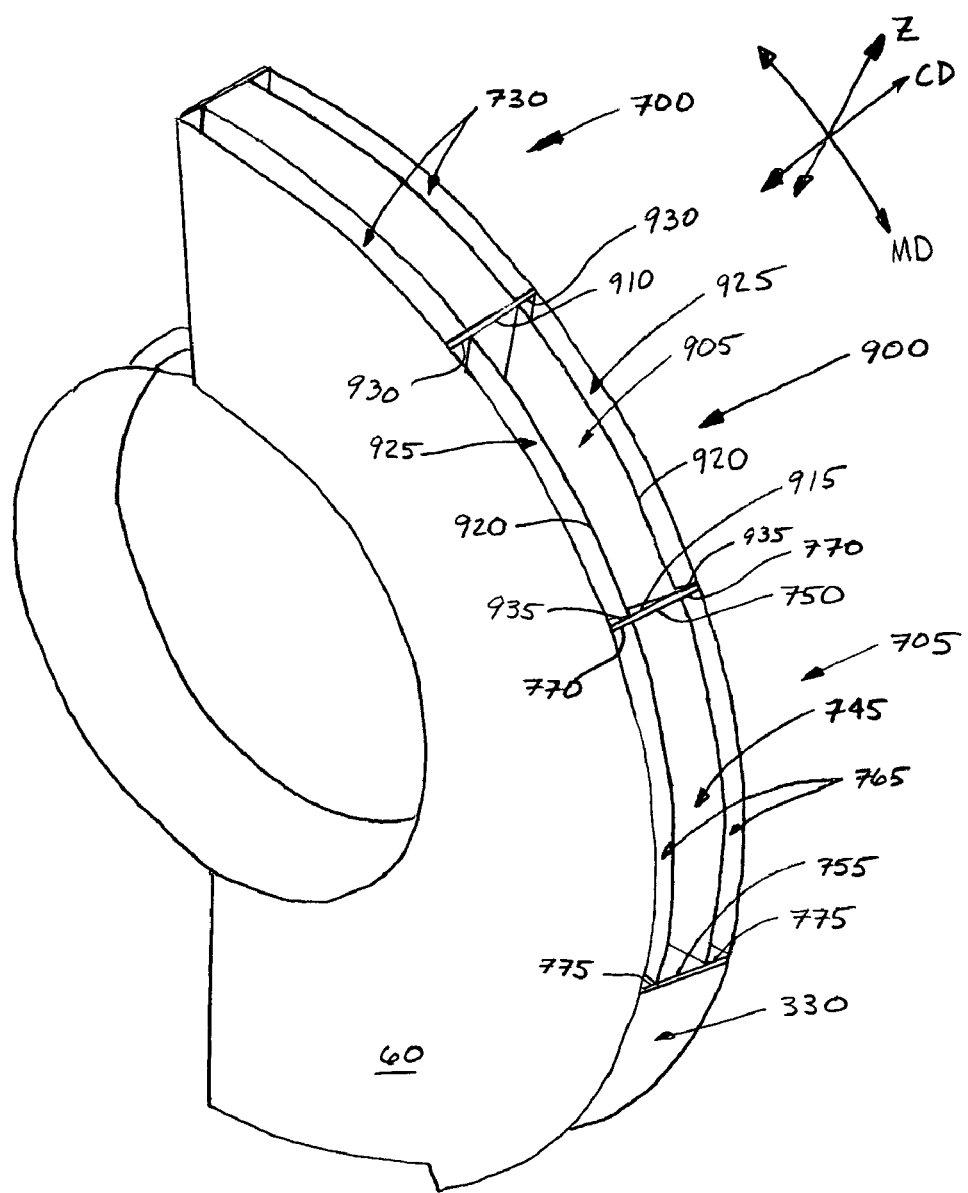
FIG. 13 is a perspective view of one embodiment of an air-distribution manifold.

In another embodiment of the apparatus 10, the air-distribution manifold 60 can comprise a cleaning area 900 between the first forming area 700 and the second forming area 705, as shown in FIG. 13. The cleaning area 900 can comprise a central cleaning zone 905. The central cleaning zone 905 can have a central cleaning zone first end 910, a central cleaning zone second end 915 opposing the central cleaning zone first end 910, and a pair of opposing central cleaning zone lateral side edges 920 extending from the central cleaning zone first end 910 to the central cleaning zone second end 915. The central cleaning zone second end 915 can be adjacent the second central zone first end 750. The air-distribution manifold 60 can further comprise a pair of edge cleaning zones 925, each of the edge cleaning zones 925 being adjacent a central cleaning zone lateral side edge 920. The edge cleaning zones 925 can each have an edge cleaning zone first end 930 and an edge cleaning zone second end 935 opposing the edge cleaning zone first end 930.

In the embodiment of the air-distribution manifold 60 shown in FIG. 13, the air-distribution manifold can further comprise a first forming area 700. The first forming area 700 can comprise a pair of first edge zones 730. Each of the first edge zones 730 can be adjacent an edge cleaning zone first end 930. In the embodiment shown in FIG. 12, a portion of the air-distribution manifold 60 between the first edge zones 730 can be inactive, meaning that air flow does not occur through this portion of the air-distribution manifold 60.

In one embodiment of the apparatus 10, the air-distribution manifold 60 illustrated in FIG. 13 can be configured as follows to permit laying an island of one kind of fibrous material that is surrounded in-plane (the MD-CD plane) by a ring of fibers of a different kind. The pressure in the first edge zones 730 can be negative. The pressure on the surface of the air-distribution manifold 60 between the first edge zones 730 can be ambient. In this configuration, a stream of loose air-entrained first fibers 12 can be provided. The core pocket 50 can be provided in operative relationship with the stream of loose air-entrained first fibers 12. First fibers 12 can be drawn to and deposited on the edge foraminous forming surface 195 of the core pocket 50. Since, the pressure on the surface of the air-distribution manifold 60 between the first edge zones 730 is ambient, little or no first fibers 12 are deposited on the central foraminous forming surface 180.

As the core pocket 50 moves to the cleaning area 900, first fibers 12 that were misdirected or misdrawn and deposited on the central foraminous forming surface 180 can be cleaned from the central foraminous forming surface 180. In the cleaning area 900, the pressure in the central cleaning zone 905 can be positive or ambient and the pressure in the edge cleaning zones 925 can be negative. The pressure in the central cleaning zone 905 can be negative but greater than the pressure in the edge cleaning zones 925. In any of these configurations, the positive pressure in the central cleaning zone 905 and/or air drawn from the central cleaning zone 905 by the edge cleaning zones 925 can dislodges and re-suspends first fibers 12 lying on the central foraminous forming surface 180 and the negative pressure in the edge cleaning zones 925 draws the re-suspended first fibers 12 to the edge foraminous forming surface 195.

As the core pocket 50 moves to the second forming are 705, the pressure in the second central zone 745 can be negative and the pressure in the second edge zones 765 can also be negative. In this configuration, a stream of loose air-entrained second fibers 612 can be provided. The core pocket 50 can be provided in operative relationship with the stream of loose air-entrained second fibers 612. In this configuration, second fibers 612 are drawn to and deposited on the central foraminous forming surface 180.

The negative pressure in the second edge zones 765 should be sufficient to hold down the first fibers 12 deposited on the edge foraminous forming surface 195 but not be so negative such that ring of first fibers 12 is adversely affected by the negative pressure. Furthermore, the negative pressure in the second edge zones 765 should not be so negative such that second fibers 612 are drawn on top of the ring of first fibers 12 on the edge foraminous forming surface 195. For an air-distribution manifold 60 configured as shown in FIG. 13, the pressure in the second central zone 745 can be negative and less than the pressure in the second edge zones 765.

Figure 14:
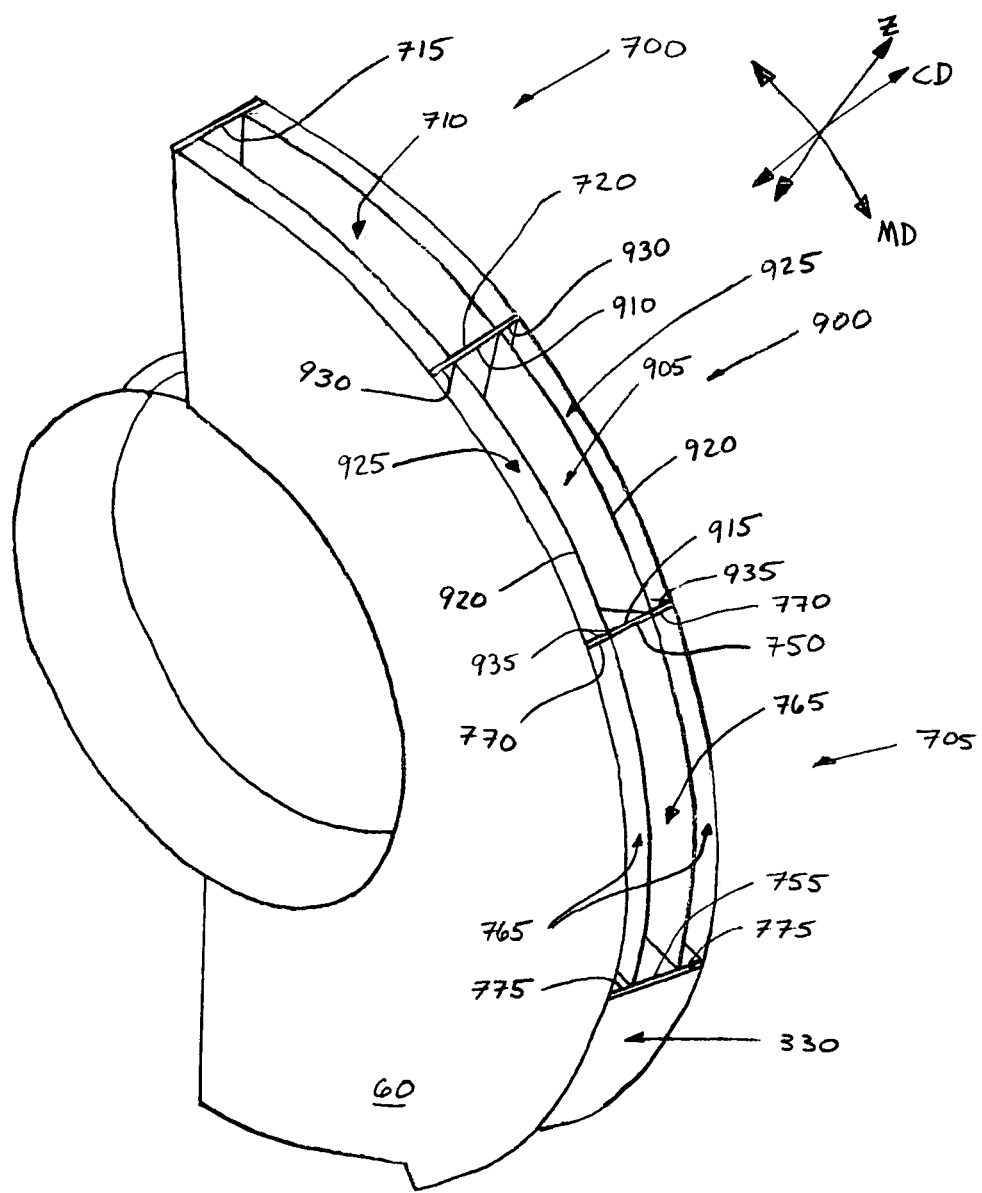
FIG. 14 is a perspective view of one embodiment of an air-distribution manifold.

In another embodiment of the apparatus 10, the air-distribution manifold 60 can comprise a cleaning area 900 between the first forming area 700 and the second forming area 705, as shown in FIG. 14. In the embodiment of the air-distribution manifold 60 shown in FIG. 14, the air-distribution manifold can further comprise a first forming area 700. The first forming area 700 can comprise a first central zone 710. The first central zone 710 can have a first central zone first end 715 and a first central zone second end 720 opposing the first central zone first end 715. In the embodiment shown in FIG. 14, the portions of the air-distribution manifold 60 laterally adjacent in the cross direction to the first central zone 710 are inactive, meaning that air flow does not occur through these portions of the air-distribution manifold 60. The pressure in the portion of the air-distribution manifold 60 laterally adjacent in the cross direction to the first central zone 710 can be ambient. If ambient pressure is employed, air drawn through the edge foraminous forming surface 195 substantially impede deposition of first fibers 12 onto the edge foraminous forming surface 195 and can dislodge and re-suspend first fibers 12 lying on the edge foraminous forming surface 195. The negative pressure in the first central zone 710 can draw the redirected and/or re-suspended first fibers 12 to the central foraminous forming surface 180.

In one embodiment of the apparatus 10, the air-distribution manifold 60 illustrated in FIG. 14 can be configured as follows to permit laying an island of one kind of fibrous material that is surrounded in-plane (the MD-CD plane) by a ring of fibers of a different kind. In this configuration, a stream of loose air-entrained first fibers 12 can be provided. The core pocket 50 can be provided in operative relationship with the stream of loose air-entrained first fibers 12. First fibers 12 can be drawn to and deposited on the central foraminous forming surface 180 of the core pocket 50. Since, the pressure on the edge foraminous forming surface 195 is ambient, little or no first fibers 12 are deposited on the edge foraminous forming surface 195.

As the core pocket 50 moves to the cleaning area 900, first fibers 12 the were misdirected or misdrawn and deposited on the edge foraminous forming surface 195 can be cleaned from the edge foraminous forming surface 195. In the cleaning area 900, the pressure applied to the central foraminous forming surface 180 at the central cleaning zone 905 can be negative and the pressure applied to the edge foraminous forming surface 195 at the edge cleaning zones 925 can be positive, ambient, or negative but greater than the pressure at the central cleaning zone 905. In this configuration, the positive pressure in the edge cleaning zones 925 or air drawn from the edge cleaning zones 925 can dislodge and re-suspend first fibers 12 lying on the edge foraminous forming surface 195 and the negative pressure in the central cleaning zone 905 can draw the re-suspended first fibers 12 to the central foraminous forming surface 180.

As the core pocket 50 moves to the second forming are 705, the pressure in the second central zone 745 can be negative and the pressure in the second edge zones 765 can also be negative. In this configuration, a stream of loose air-entrained second fibers 612 can be provided. The core pocket 50 can be provided in operative relationship with the stream of loose air-entrained second fibers 612. In this configuration, second fibers 612 are drawn to and deposited on the edge foraminous forming surface 195.

The negative pressure in the second central zone 745 should be sufficient to hold down the first fibers 12 deposited on the central foraminous forming surface 180 but not be so negative such that the structure of the island of first fibers 12 is adversely affected by the negative pressure. Furthermore, the negative pressure in the second central zone 745 should not be so negative such that second fibers 612 are drawn on top of the island of first fibers 12 on the central foraminous forming surface 180. For an air-distribution manifold 60 configured as shown in FIG. 14, the pressure in the second edge zones 765 can be negative and less than the pressure in the second central zone 745.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for forming air-laid fibrous articles comprising:
   a core pocket and an air-distribution manifold operatively related to said core pocket, said core pocket comprising:
     a shield having an interior facing surface, an exterior facing surface, a shield first end, a shield second end opposing said shield first end, and a pair of opposing shield lateral side edges extending from said shield first end to said shield second end;
     a central opening defined by a void in said shield;
     a central forming chamber in air-flow communication with said central opening and having a central forming chamber periphery;
     a central foraminous forming surface in air-flow communication with said central forming chamber;
     a pair of edge openings extending along said shield and extending laterally beyond said shield lateral side edges;
     an edge forming chamber disposed about said central forming chamber periphery and in air-flow communication with said edge openings; and
     an edge foraminous forming surface in air-flow communication with said edge forming chamber;
   said air-distribution manifold comprising a second forming area, said second forming area comprising:
     a second central zone, said second central zone having a second central zone first end, a second central zone second end opposing said second central zone first end, and a pair of opposing second central zone lateral side edges extending from said second central zone first end to said second central zone second end; and
     a pair of second edge zones, each of said second edge zones adjacent a second central zone lateral side edge.

2. The apparatus of claim 1, wherein said core pocket further comprises a plurality of central lateral baffles, said central lateral baffles spanning said central forming chamber and aligned about flush with said interior facing surface of said shield.

3. The apparatus of claim 1, wherein said core pocket further comprises a plurality of edge lateral baffles, said edge lateral baffles spanning said edge forming chamber and aligned about flush with said interior facing surface of said shield.

4. The apparatus of claim 1 wherein said second central zone and said second edge zones are under pressure and the pressure in said second central zone is negative and less than the pressure in said second edge zones.

5. The apparatus of claim 1 wherein said second central zone and said second edge zones are under pressure and the pressure in said second edge zones is negative and less than the pressure in said second central zone.

6. The apparatus of claim 1 wherein said air-distribution manifold further comprises a first forming area, said first forming area comprising:

a first central zone, said first central zone having a first central zone first end, a first central zone second end opposing said first central zone first end, and a pair of opposing first central zone lateral side edges extending from said first central zone first end to said first central zone second end wherein said first central zone second end is adjacent said second central zone first end; and
   a pair of first edge zones, each of said first edge zones adjacent a first central zone lateral side edge.

7. The apparatus of claim 6 wherein said first central zone and said first edge zones are under pressure and the pressure in said first central zone is negative and the pressure in said first edge zones is positive.

8. The apparatus of claim 6 wherein said first central zone and said first edge zones are under pressure and pressure in said first central zone is positive and the pressure in said first edge zones is negative.

9. The apparatus of claim 1, wherein said air-distribution manifold further comprises a cleaning area, said cleaning area comprising:

a central cleaning zone, said central cleaning zone having a central cleaning zone first end, a central cleaning zone second end opposing said central cleaning zone first end, and a pair of opposing central cleaning zone lateral side edges extending from said central cleaning zone first end to said central cleaning zone second end, wherein said central cleaning zone second end is adjacent said second central zone first end; and
   a pair of edge cleaning zones, each of said edge cleaning zones adjacent a central cleaning zone lateral side edge.

10. The apparatus of claim 9 wherein said central cleaning zone and said edge cleaning zones are under pressure and the pressure in said central cleaning zone is positive and the pressure in said edge cleaning zones is negative.

11. The apparatus of claim 9 wherein said central cleaning zone and said edge cleaning zones are under pressure and the pressure in said central cleaning zone is negative and the pressure in said edge cleaning zones is positive.

12. The apparatus of claim 9 wherein said air-distribution manifold further comprises a first forming area, said first forming area comprising a first central zone, said first central zone having a first central zone first end, a first central zone second end opposing said first central zone first end, and a pair of opposing first central zone lateral side edges extending from said first central zone first end to said first central zone second end, wherein said first central zone second end is adjacent said central cleaning zone first end.

13. The apparatus of claim 12 wherein said first central zone is under pressure and the pressure in said first central zone is negative.

14. The apparatus of claim 9 wherein said edge cleaning zones have an edge cleaning zone first end and an edge cleaning zone second end opposing said edge cleaning zone first end, wherein said air-distribution manifold further comprises a first forming area, said first forming area comprising a pair of first edge zones, each of said first edge zones adjacent an edge cleaning zone first end.

15. The apparatus of claim 14 wherein said first edge zones are under pressure and the pressure in said first edge zones is negative.

16. The apparatus of claim 1 further comprising a first discharge chute that discharges first fibers and a second discharge chute that discharges second fibers wherein said first fibers differ from said second fibers, said first discharge chute and said second discharge chute operatively related to said core pocket and said air-distribution manifold.

17. The apparatus of claim 16, wherein said first fibers and said second fibers differ from one another in terms of their fluid handling properties.

18. The apparatus of claim 16, wherein said first fibers and said second fibers differ from one another in a manner selected from the group consisting of color, a tactile property, and a mechanical property.

19. The apparatus of claim 1, wherein said core pocket is shaped to form an absorbent article designed to be worn in proximity to the crotch of a wearer.

20. The apparatus of claim 1, wherein said core pocket is shaped to form the core of a sanitary napkin.

* * * * *

UNITED STATES PATENT AND TRADEMARK OFFICE
CERTIFICATE OF CORRECTION

PATENT NO. : 7,549,853 B2  Page 1 of 1
APPLICATION NO. : 11/599820
DATED : June 23, 2009
INVENTOR(S) : Fegelman et al.

It is certified that error appears in the above-identified patent and that said Letters Patent is hereby corrected as shown below:

Title Page Other Publications

Section (56) – References Cited, in the reference for U.S. Appl. No. 11/599,789 delete "25006" and insert --2006--.

Column 10

Line 66, delete the number "4" that is in front of the word metal.

Signed and Sealed this

Third Day of November, 2009

David J. Kappos
*Director of the United States Patent and Trademark Office*